United States Patent
Ficko Trcek

(10) Patent No.: US 9,562,082 B2
(45) Date of Patent: Feb. 7, 2017

(54) PRODUCTION OF GLYCOPROTEINS WITH LOW N-GLYCOLYLNEURAMINIC ACID (NEU5GC) CONTENT

(71) Applicant: LEK Pharmaceuticals D.D., Ljubljana (SI)

(72) Inventor: Tanja Ficko Trcek, Menges (SI)

(73) Assignee: LEK PHARMACEUTICALS D.D., Ljubljana (SI)

( * ) Notice: Subject to any disclaimer, the term of this patent is extended or adjusted under 35 U.S.C. 154(b) by 0 days.

(21) Appl. No.: 14/280,216

(22) Filed: May 16, 2014

(65) Prior Publication Data

US 2014/0288281 A1 Sep. 25, 2014

Related U.S. Application Data

(62) Division of application No. 13/503,254, filed as application No. PCT/EP2010/067793 on Nov. 19, 2010, now Pat. No. 8,728,816.

(30) Foreign Application Priority Data

Nov. 20, 2009 (EP) ..................................... 09176631

(51) Int. Cl.
    *C12N 5/00* (2006.01)
    *C07K 14/47* (2006.01)
    *C12P 21/00* (2006.01)

(52) U.S. Cl.
    CPC ............. *C07K 14/47* (2013.01); *C12N 5/0018* (2013.01); *C12P 21/005* (2013.01); *C12N 2500/20* (2013.01); *C12N 2500/30* (2013.01); *C12N 2500/34* (2013.01); *C12N 2500/62* (2013.01)

(58) Field of Classification Search
    CPC ................................ C07K 14/47; C12P 21/005
    See application file for complete search history.

(56) References Cited

U.S. PATENT DOCUMENTS

| 5,459,031 | A | 10/1995 | Blumen et al. |
| 2007/0161084 | A1 | 7/2007 | Crowell et al. |

FOREIGN PATENT DOCUMENTS

| EP | 1 092 037 | 4/2001 |
| EP | 1 543 106 | 6/2005 |
| WO | WO 2008/128227 | 10/2008 |

OTHER PUBLICATIONS

Kimura et al., Glycosylation of CHO-derived recombinant tPA produced under elevated pCO2. Biotechnology Progress, vol. 13 (1997) pp. 311-317.*
Borys et al., Effects of culture conditions on N-glycollylneuraminic acid (Neu5Gc) content of a recombinant fusion protein produced in CHO cells. Biotechnology and Bioengineering, vol. 105, No. 6 (online Dec. 28, 2009) pp. 1048-1057.*
Bork et al., "Increasing the sialylation of therapeutic glycoproteins: the potential of the sialic acid biosynthetic pathway," *Journal of Pharmaceutical Sciences*, 98(10):3499-3508, 2009.
Chenu et al., "Reduction of CMP-N-acetylneuraminic acid hydroxylase activity in engineered Chinese hamster ovary cells using an antisense-RNA strategy," *Biochimica et Biophysica Acta*, 1622(2):133-144, 2003.
Fibach et al., "Changes in cellular ferritin content during myeloid differentiation of human leukemic cell lines," *American Journal of Hematology*, 18(2):143-151, 1985.
Gu and Wang, "Improvement of interferon-γ sialylation in Chinese hamster ovary cell culture by feeding of n-acetylmannosamine," *Biotechnology and Bioengineering*, 58(6):642-648, 1998.
Liu and Chen, "Promotion of recombinant macrophage colony stimulating factor production by dimethyl sulfoxide addition in Chinese hamster ovary cells," *Journal of Bioscience and Bioengineering*, 103(1):45-49, 2007.
Office Communication issued in U.S. Appl. No. 13/503,254, dated Nov. 25, 2013.
Office Communication issued in U.S. Appl. No. 13/503,254, dated Jun. 18, 2013.
Office Communication issued in U.S. Appl. No. 13/503,254, dated Dec. 21, 2012.
Office Communication issued in U.S. Appl. No. 13/503,254, dated Nov. 7, 2012.
PCT International Search Report and Written Opinion issued in International application No. PCT/EP2010/067793, dated Jan. 24, 2011.
Rodriguez et al., "Enhanced production of monomeric interferon-[beta] by CHO cells through control of culture conditions," *Biotechnology Progress*, 21(1):22-30, 2005.
Traving and Schauer, "Structure, function and metabolism of sialic acids," *Cell. Mol. Life Sci.*, 54(12):1330-1349, 1998.
Yamaguchi et al., "Simple and large-scale production of n-acetylneuraminic acid and n-acetyl-d-mannosamine," *Trends in Glysoscience and Glycotechnology*, 18:245-252, 2006.
Llop et al., "Structural analysis of the glycosylation of gene-activated erythropoietin (epoetin delta, Dynepo)," *Analytical Biochemistry*, 383: 243-254, 2008.

* cited by examiner

*Primary Examiner* — Kara Johnson
(74) *Attorney, Agent, or Firm* — Parker Highlander PLLC

(57) ABSTRACT

The present invention relates to a medium for the cultivation of eukaryotic cells, the medium comprising as (an) additive(s) DMSO, N-acetylmannosamine (NAcMan), N-acetylglucosamine (NAcGlc), or any combination of two or more of these additives, including the combination of NAcMan and NAcGlc.

17 Claims, 11 Drawing Sheets

Fig. 4a  Growth curves
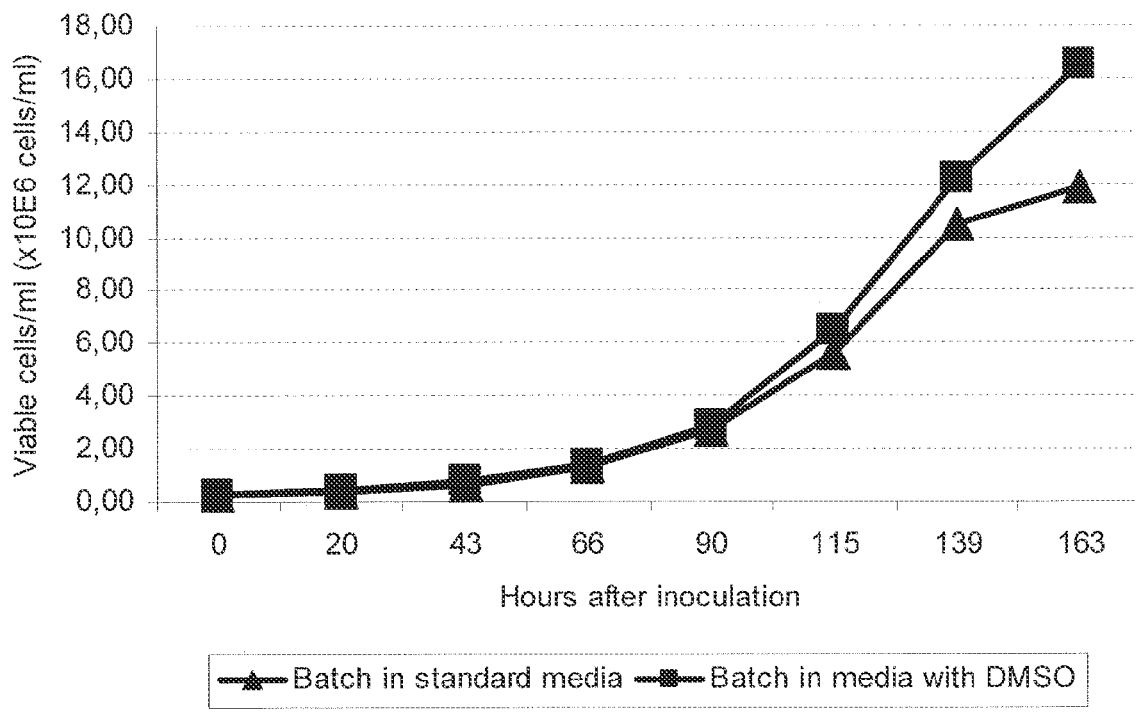
Fig. 4b
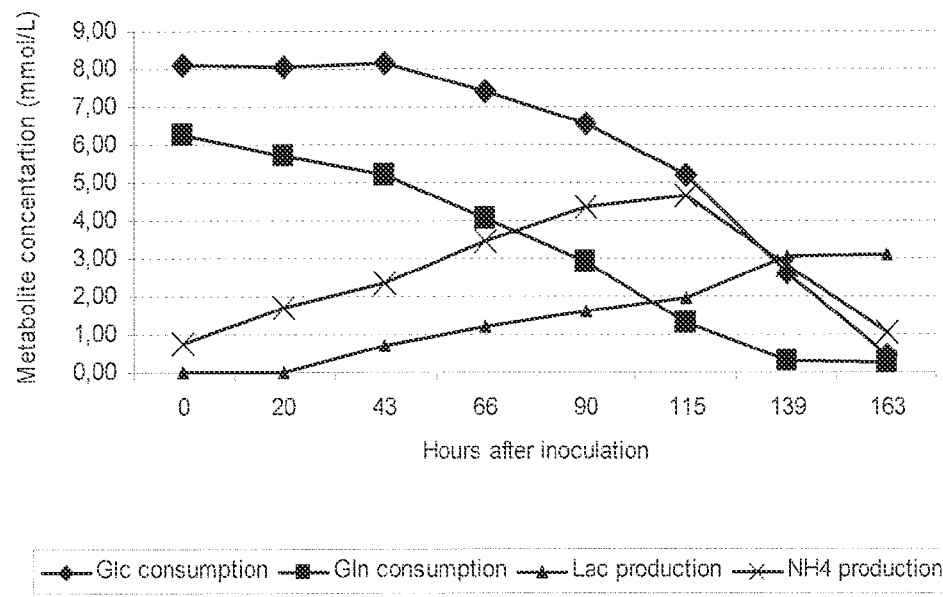

Fig. 11a  Percent of the most acidic isoforms (isoforms 7&8)
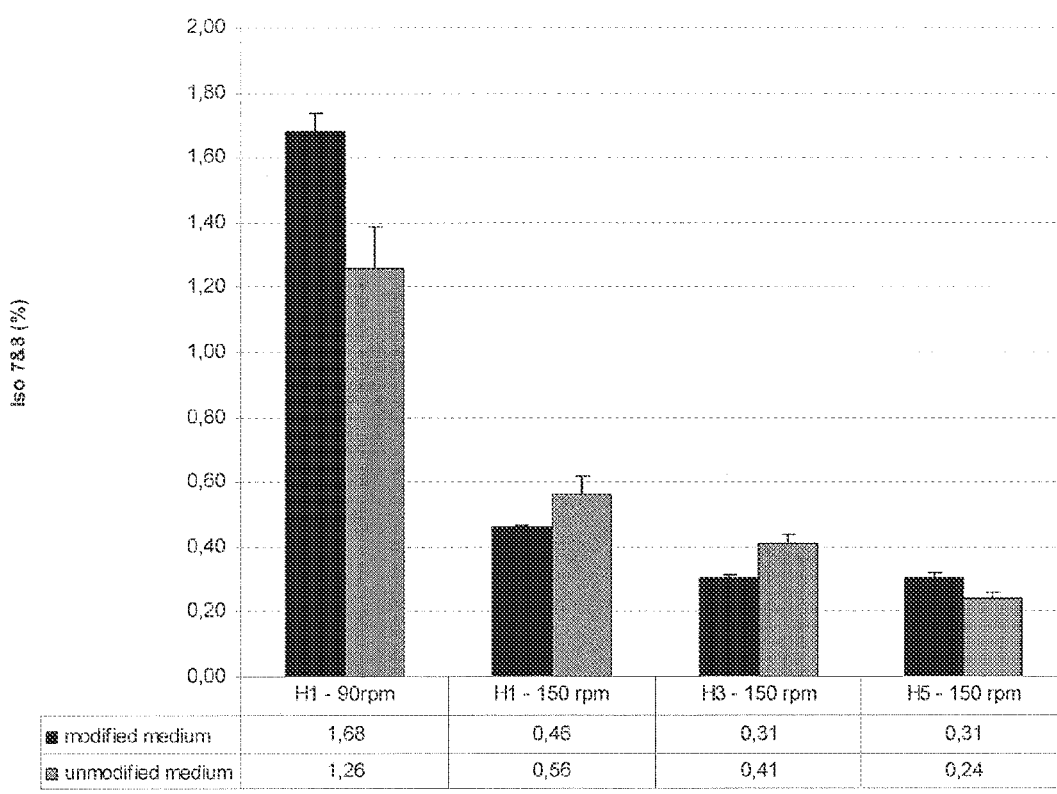
Fig. 11b  Content of Neu5Gc
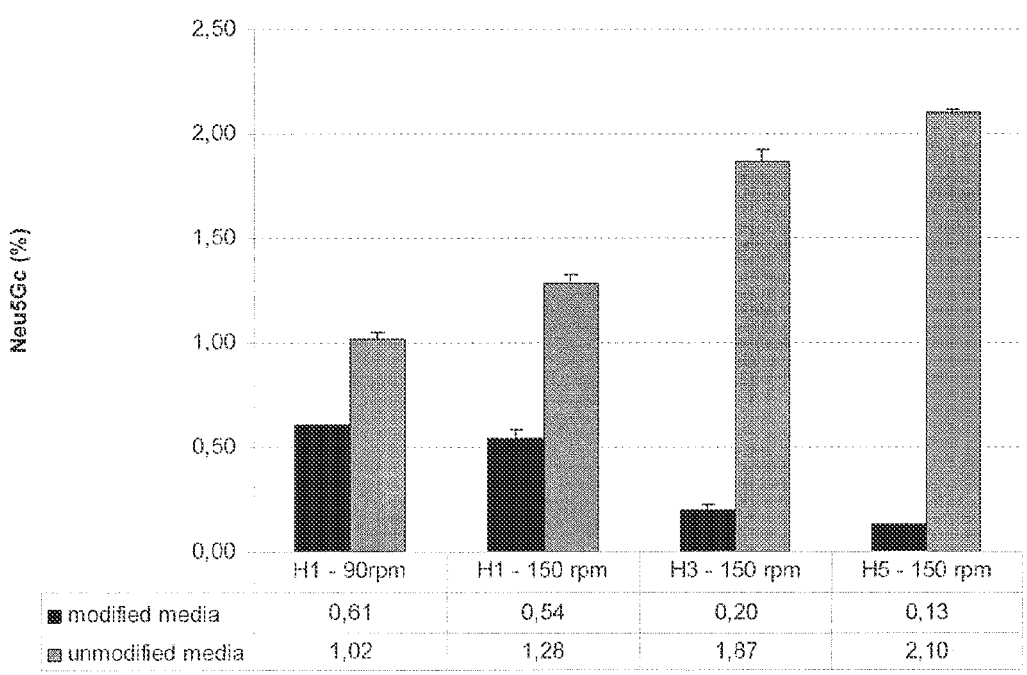

PRODUCTION OF GLYCOPROTEINS WITH LOW N-GLYCOLYLNEURAMINIC ACID (NEU5GC) CONTENT

CROSS-REFERENCE TO RELATED APPLICATIONS

This application is a divisional of U.S. application Ser. No. 13/503,254, which was filed as a national phase application under 35 U.S.C. §371 of International Application No. PCT/EP2010/067793 filed 19 Nov. 2010, which claims priority to European Application No. 09 176 631.1 filed on 20 Nov. 2009. The entire text of each of the above-referenced disclosures is specifically incorporated herein by reference without disclaimer.

BACKGROUND OF THE INVENTION

1. Field of the Invention

The present invention relates to a method of preparing glycoproteins, in particular recombinant glycoproteins, having a high degree of sialylation but a low content of N-glycolylneuraminic acid (Neu5Gc). The method includes the cultivation of cells, in particular host cells, in the presence of (a) dimethyl sulfoxide (DMSO), (b) N-acetylmannosamine (NAcMan), (c) N-acetylglucosamine (NAcGlc), or (d) any combination of two or more thereof. That is, according to the present invention DMSO, NAcMan, and NAcGlc are used as cell culture medium additives.

2. Description of Related Art

Approximately 50% of the proteins produced in eukaryotic cells are glycosylated, which means that they are modified with one ore more oligosaccharide group(s). Usually said glycosylation occurs in two types: O-linked oligosaccharides (attached to serine or threonine residues of the polypeptide backbone) and N-linked oligosaccharides (attached to asparagine residues present within a specific target sequence). The glycosylation profile of these glycoproteins is essential to ensure structural, biological, and clinical stability. Glycosylation of therapeutic proteins plays an essential role in pharmacokinetics, pharmacodistribution, protection from proteolytic degradation, solubility, and receptor binding (Werner et al., 2007). A high degree of terminal sialylation of glycans is important in therapeutic glycoproteins in order to avoid the effect of asialoglycoprotein receptors present in the liver and macrophages, which receptors cause the removal of the glycoproteins from the circulatory system, unless they are sialylated. However, it is desirable that the content of one specific representative (N-glycolylneuraminic acid, Neu5Gc) making up and contributing to sialylation in glycoproteins is low relative to the principal sialic acid (N-acetylneuraminic acid, Neu5Ac) and all other sialic acids (for more details, see below). Thus, there are "good" sialic acids, the principal representative being Neu5Ac, and one "bad" sialic acid: Neu5Gc.

Sialylation is the last intracellular stage of the glycosylation process and involves the enzymatic transfer of sialic acid from a nucleotide sugar precursor, CMP sialic acid, to a galactose moiety available on the emerging glycan structure that is attached to the newly synthesised protein. By the introduction of new or additional N-linked glycosylation sites into the polypeptide backbone, it is possible to create therapeutic glycoproteins that contain additional oligosaccharides which lead to an increased sialic acid content. These proteins show a prolonged serum half-life and an increased biological activity.

Sialic acids compose a family of about 40 derivates of neuraminic acid, which is a nine-carbon atom sugar (e.g., Schauer, 2000). The amino group at position 5 of neuraminic acid is usually acetylated, and this leads to N-acetylneuraminic acid (Neu5Ac), the most widespread form of sialic acids, as mentioned above. A high degree of sialylation of a glycoprotein is thus tantamount to a high degree of Neu5Ac in the glycoprotein and, due to the carboxylic acid function in the neuraminic acid derivatives, also tantamount to an increased acidity of the glycoprotein: the higher the degree of sialylation, the more acidic is the isoform of the glycoprotein.

One of the common modifications of Neu5Ac is the substitution of one of the hydrogen atoms of the acetyl group by a hydroxyl group ($-(O=)C-CH_3 \rightarrow -(O=)C-CH_2OH$). The substitution is regulated by the enzyme cytidine-5'-monophosphate-N-acetylneuraminic acid hydroxylase (CMP-Neu5Ac hydroxylase) and results in N-glycolylneuraminic acid (Neu5Gc), commonly found in many animal species, but never in normal chicken and human tissues (e.g., Corfield and Schauer, 1982). CMP-Neu5Ac hydroxylase was found to be attached to the surface of the nucleus and to some neighbouring microsomes, and the conversion of Neu5Ac into potentially immunogenic Neu5Gc to take place in the cytosol after CMP-Neu5Ac synthesis in the nucleus.

The catalytic properties including inhibition of CMP-Neu5Ac hydroxylase in vitro have been studied. CMP-Neu5Ac hydroxylase is markedly inhibited by a relatively small increase of the ionic strength. 80% inhibition was obtained with $Cu^{2+}$, 50% inhibition with $Ni^{3+}$, $Mn^{2+}$, and $Co^{2+}$, and 30% inhibition with $Zn^{2+}$. Inhibition studies using iron and other metal ligands were also performed obtaining 60% inhibition with the metal ion chelator EDTA. 100% inhibition was accomplished with the iron chelator tiron, 25% inhibition with the iron chelator ferozzine, and 25% inhibition with the zinc chelator phenanthreoline. One scientific paper reported that the only possibility for regulating the proportion of Neu5Gc in the sialic acid pool is to change the activity of CMP-Neu5Ac hydroxylase (Traving and Schauer, 1998).

The immunological implications of Neu5Gc in humans are not fully understood, but it is well known in the art that an increase in the Neu5Gc content of glycoproteins correlates with enhanced antigenicity and, in particular, immunogenicity of the glycoproteins, an undesirable feature for therapeutic proteins. As chickens do not possess Neu5Gc, they were used to shed light on its possible immunogenicity. For example, recombinant human erythropoietin (rhEPO) produced by Chinese hamster ovary (CHO) cells has been reported to contain small amounts (1% of total sialic acids) of Neu5Gc (throughout the entire description below including the examples, any % data for the Neu5Gc content is % (w/w) and refers to the amount of Neu5Gc relative to the total amount of sialic acids in the respective glycoprotein). Though chickens immunised with rhEPO did not produce a significant titre of a respective antibody, a significant titre of antibodies against Neu5Gc was obtained from chickens immunised with (i) fetuin (which has a content of Neu5Gc amounting to 7%) and (ii) GM3 with no Neu5Ac moieties at all (because all Neu5Ac moieties attached to the protein had been converted into Neu5Gc). Therefore, it is readily apparent that the prime objectives for the pharmaceutical industry producing glycoprotein biopharmaceuticals is (i) to keep the content of Neu5Gc as low as possible, preferably below 1%, more preferably even below 0.8%, (ii) to closely monitor the Neu5Gc levels of the glycoprotein biopharmaceutical, and optionally (iii) to reduce the Neu5Gc content of the glycoprotein biopharmaceutical.

Methods and strategies to increase the efficiency of recombinant protein production have been described in the art. Amongst others, butyric acid, glycerol, and dimethyl sulfoxide (DMSO), if added to a CHO cell culture, were found to improve productivity of the protein production process. Simultaneously, these chemicals also induced G0/G1 phase growth arrest and cell growth cessation. Also, DMSO as a cell culture additive (partially) arrests the cells in the G0/G1 phase of the cell cycle, promotes proper protein folding, and enhances protein synthesis.

The literature likewise describes methods to increase the degree of glycosylation and sialylation of recombinant proteins. For example, EP-B 1 543 106 describes a method for increasing the degree of sialylation of glycoproteins produced by mammalian cells. The cell culture medium is supplemented with the key intermediates of the metabolic pathway leading to sialylation of proteins. A combination of galactose (Gal, preferably 0.1 to 40 mM) and fructose (Fru, preferably 1 to 10 mM), with or without mannose (Man, preferably 0.5 to 20 mM, if added) and N-acetylmannosamine (NAcMan, preferably 0.8 to 4 mM, if added) were employed, resulting in an increase of the degree of sialylation.

Another report, Gu and Wang (1998), describes the increase of the intracellular pool of CMP-sialic acid, i.e., the nucleotide sugar substrate for sialylatransferase and, as a consequence thereof, a 15% increase of sialylated interferon-γ was observed.

Yamaguchi et al. (2006) teach that NAcMan is a Neu5Ac (sialic acid) precursor and can be fed to protein-expressing cells to maximise the final sialic acid content of a glycoprotein. In this respect, the authors disclose a large-scale method for NAcMan production from Neu5Ac. Another cell culture process for the production of glycoproteins with increased sialic acid content is set out in EP-B 1 092 037. The experimentators added copper ions to the cell culture in a concentration effective to stabilise the sialic acid content.

A number of enzymes involved in glycosylation (dolichol-linked oligosaccharide synthesis, enzymes that catalyse the addition of O-linked carbohydrates, β-galactoside-α-1,3-galactosyltransferase) utilise divalent cations (e.g. $Mn^{2+}$) as co-factors. The use of manganese in a concentration of 0.01 µM to 40 µM is described in US-A 2007/0161084 as a method for improving glycosylation and sialylation of glycoproteins.

Finally, U.S. Pat. No. 5,459,031 describes a method for decreasing the Neu5Gc content in proteins by manipulating the culture environment in a way as to increase the concentration of dissolved carbon dioxide and/or carbonate species. The authors managed to control the amount of sialic acid derivates on recombinant glycoproteins and to decrease the Neu5Gc level on the native or recombinant proteins.

As shown above, there is literature available addressing an increase of the degree of sialylation, which means in particular an increase of the Neu5Ac content. However, an increased Neu5Ac content can also lead to an increased Neu5Gc content which is quite undesirable for therapeutic glycoproteins (see above). Only U.S. Pat. No. 5,459,031 describes a method for the production of highly sialylated recombinant glycoproteins with low levels of Neu5Gc. However, according to said patent the content of Neu5Gc is controlled by adjusting and monitoring the level of $CO_2$ in a reaction mixture during protein biosynthesis. Since it is difficult to control the level of $CO_2$ in simple batch and fed batch processes, that method would appear to be limited to repeated batch and perfusion processes.

To summarise the prior art, in particular that described above, there is only limited literature available that is focusing directly on the production of (recombinant) glycoproteins exhibiting a low Neu5Gc content. Accordingly, there is a need for a fast, easy, and cost-effective method that is easily applicable also in a batch and fed batch process to achieve (and maintain) an increased degree of sialylation in (therapeutic) glycoproteins, while the content of (antigenic and thus unwanted) Neu5Gc on said glycoproteins is concomitantly decreased or maintained at low levels.

SUMMARY OF THE INVENTION

Based on the above described localisation of (i) the CMP-Neu5Ac hydroxylase (on the surface of the nucleus and on microsomes) and of (ii) the Neu5Ac→Neu5Gc conversion (cytosol), the present inventor assumed that expression of CMP-Neu5Ac hydroxylase occurs after Neu5Ac synthesis, and probably during S phase of the cell cycle. Based on this assumption, a shortened (i.e., limited) duration of the S phase of the cell cycle on account of a prolonged G0/G1 phase was expected to lead to a decreased period of CMP-Neu5Ac hydroxylase expression and, consequently, also to a decreased CMP-Neu5Ac hydroxylase concentration. The inventor did not know, however, the impact, if any, DMSO might have on the sialic acid content of the glycoproteins to be expressed.

The inventor concluded that DMSO in the culture medium might entail, by arresting and synchronising the cells in the G0/G1 phase, an increased degree of sialylation, a decreased expression of CMP-Neu5Ac hydroxylase, and a decreased content of Neu5Gc on the glycoprotein(s) to be expressed. In fact, these goals were achieved, probably due to an enhanced expression/action of the sialyltransferase(s) and a lower or limited expression/action of CMP-Neu5Ac hydroxylase. Both shake flask and 5 litre-bioreactor experiments run in batch mode demonstrate a decreased Neu5Gc content in the glycoproteins produced.

Based on the importance of the CMP-sialic acid pool (i.e., the nucleotide sugar substrate for sialylatransferase) in trans-Golgi and the lack of knowledge of its effect on CMP-Neu5Ac hydroxylase activity, the inventor additionally tested the effect of NAcMan and NAcGlc in cell culture media on the conversion of Neu5Ac to Neu5Gc and found results similar to that when employing DMSO: degree of sialylation was increased, expression of CMP-Neu5Ac hydroxylase was decreased as was the content of Neu5Gc on the glycoprotein(s).

Accordingly, the present invention solves the above problem and provides a method with unlimited applicability to achieve (and maintain) an increased degree of sialylation of (therapeutic) glycoproteins while the content of (unwanted) Neu5Gc of said glycoproteins is concomitantly decreased (or kept at a low level). Said antipodal regulation of distinct sialic acid species is achieved by adding DMSO, NAcMan, NAcGlc, or any combination of two or more thereof to the cell culture media used for fermentation. Hence, the present invention provides a fast, easy, and cost-effective method for the production of glycoproteins (the glycoproteins having a high degree of sialylation while simultaneously having a beneficially low Neu5Gc content) for use in all conceivable bioprocesses.

Throughout the entire description, above and below and including the examples, unless explicitly stated otherwise, the degree of sialylation is given in % (w/w) and was calculated as follows. Since the inventor had not available a method to directly measure the degree of sialylation (%, w/w), she estimated same indirectly from the relative content of the most acidic isoforms of each glycoprotein. Since isoforms 7 and 8 (see next paragraph) are the most acidic ones, she figured out that an increase of isoforms 7 and 8 is an indicator for the increased degree of sialylation.

The inventor measured the distribution of the isoforms of a particular glycoprotein (e.g., of darbepoetin alfa, which is a cytokine) with AEX (anion exchange chromatography). AEX is not a quantitative method. Therefore, the inventor split the histogram into three parts as follows: the most basic isoforms 1, 2, and 3, the middle acidic isoforms 4, 5, and 6, and the most acidic isoforms 7 and 8. The most acidic isoforms 7 and 8 exhibit a higher degree of sialylation than do the other isoforms 4, 5, and 6 and a degree much higher than do isoforms 1, 2, and 3. Therefore, the inventor compared, for each glycoprotein tested, the content (%, w/w) of the most acidic isoforms resulting from media without and from media with the additives according to the invention. In case their content increased, the inventor concluded that the degree of sialylation had likewise increased. Therefore, the degree of sialylation in the present application is given as the relative content of the most acidic isoforms (%, w/w). The increase in the degree of sialylation (of a particular glycoprotein obtained from a host cell culture using a medium with the additives according to the present invention vs. that of said glycoprotein obtained from a host cell culture using a medium without the inventive additives) is given on the basis of the increase of the content of the most acidic isoforms (%) after cultivating the host cells in the presence vs. absence of said additives.

The methods and media according to the present invention are suitable for the (recombinant) production of highly sialylated monomeric and multimeric proteins, like antibodies, wherein said proteins have a reduced Neu5Gc content. Generally, (recombinant) proteins that can be produced with the methods and media of the invention include those comprising amino acid sequences identical to or substantially similar to all or part of one of the following proteins: an Flt3 ligand, a CD40 ligand, erythropoiesis stimulating proteins like erythropoietin (EPO), darbepoetin including darbepoetin alfa, and thrombopoietin, calcitonin, leptin, a Fas ligand, a ligand for receptor activator of NF-kappa B (RANKL), a tumour necrosis factor (TNF)-related apoptosis-inducing ligand (TRAIL), thymic stroma-derived lymphopoietin, granulocyte colony stimulating factor, granulocyte-macrophage colony stimulating factor (GM-CSF), growth factors including mast cell growth factor, stem cell growth factor, epidermal growth factor, keratinocyte growth factor, megakaryote growth and development factor, RANTES, growth hormone, insulin, insulinotropin, insulin-like growth factors, parathyroid hormone, interferons including α-interferon, β-interferon, and γ-interferon, nerve growth factor, brain-derived neurotrophic factor, synaptotagmin-like proteins (SLP1-5), neurotrophin-3"glucagon, interleukins including IL-1, IL-1a, IL-2, IL-3, IL-4, IL-5, IL-6, IL-7, IL-8, IL-9, IL-10, IL-11, IL-12, IL-13, IL-14, IL-15, IL-16, IL-17, and IL-18, colony stimulating factors, lymphotoxin-p, tumour necrosis factor (TNF), leukemia inhibitory factor, oncostatin-M, and various ligands for cell surface molecules ELK and Hek (such as the ligands for eph-related kinases or LERKS).

Further proteins that can be produced using the methods and media of the invention include proteins comprising all or part of the amino acid sequence of a receptor for any of the above-mentioned proteins, an antagonist to such a receptor of any of the above-mentioned proteins, and proteins substantially similar to such receptors or antagonists.

Also, proteins that can be produced using the methods and media of the invention include proteins comprising all or part of the amino acid sequences of differentiation antigens (referred to as CD proteins) or their ligands or proteins substantially similar to either of these. Examples of such antigens are differentiation antigens including CD20, CD22, CD27, CD30, CD39, CD40, and ligands thereto.

Enzymatically active proteins or their ligands can also be produced using the methods and media of the invention. Examples include proteins comprising all or part of one of the following proteins, or their ligands, or proteins substantially similar to one of these: metalloproteinase-disintegrin family members, kinases, glucocerebrosidase, superoxide dismutase, tissue plasminogen activator, Factor VIII, Factor IX, apolipoprotein E, apolipoprotein A-1, globins, an IL-2 antagonist, alpha-1 antitrypsin, TNF-alpha Converting Enzyme, ligands for any of the above-mentioned enzymes, and numerous other enzymes and their ligands.

The methods and media of the invention can also be used to produce chimeric proteins selected in vitro to bind to a specific target protein and modify its activity, and antibodies or portions thereof and chimeric antibodies, i.e. antibodies having human constant antibody immunoglobulin domains coupled to one or more murine variable antibody immunoglobulin domain, fragments thereof, or substantially similar proteins. The method of the invention may also be used to produce conjugates comprising an antibody and a cytotoxic or luminescent substance. Examples of antibodies, in vitro-selected chimeric proteins, or antibody/cytotoxin or antibody/luminophore conjugates that can be produced using the methods and media of the invention include those that recognise any one or a combination of proteins including, but not limited to, any of the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1a, IL-1, IL-2, IL-3, IL-7, IL-4, IL-5, IL-8, IL-10, IL-2 receptor, IL-4 receptor, IL-6 receptor, IL-13 receptor, IL-18 receptor subunits, PDGF-B, and analogues thereof, VEGF, TGF, TGF-β2, TGF-p1, EGF receptor VEGF receptor, hepatocyte growth factor, osteoprotegerin ligand, interferon gamma, B lymphocyte stimulator, C5 complement, IgE, tumour antigen CA125, tumour antigen MUC1, PEM antigen, ErbB2/HER-2, tumour-associated epitopes that are present in elevated levels in the sera of patients, cancer-associated epitopes or proteins expressed on breast, colon, squamous cell, prostate, pancreatic, lung, and/or kidney cancer cells and/or on melanoma, glioma, or neuroblastoma cells, the necrotic core of a tumour, integrin alpha 4 beta 7, the integrin VLA-4, B2 integrins, TRAIL receptors 1, 2, 3, and 4, RANK, a RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, MHC I, carcinoembryonic antigen (CEA), alpha-fetoprotein (AFP), tumour necrosis factor (TNF), Fc-y-1 receptor, HLA-DR 10 beta, HLA-DR antigen, L-selectin, and IFN-γ.

The methods and media of the invention can also be used to produce recombinant fusion proteins comprising any of the above-mentioned proteins or substantially similar proteins. For example, recombinant fusion proteins comprising one of the above-mentioned proteins plus a multimerisation domain, such as a leucine zipper, a coiled coil, an Fc portion of an antibody, or a substantially similar protein, can be produced using the methods and media of the invention. Specifically included among such recombinant fusion proteins are proteins in which at least a portion of TNFR or RANK is fused to an Fc portion of an antibody.

It will be understood that the skilled artisan is fully capable to determine a variety of further glycoproteins, e.g., glycoproteins containing N-linked or O-linked oligosaccharides, which are contemplated to be used in connection with the present invention.

The media used for fermentation according to the present invention support growth of the cells to very high densities. Although cell growth is somewhat reduced and the fermentation process thus slightly elongated when using a medium including the additive(s) according to the present invention, no effect on the final product titre (productivity) or on cell viability occurs. Therefore, DMSO, NAcMan and/or NAcGlc can be used for the production of high quality non-immunogenic therapeutic glycoproteins (exhibiting no Neu5Gc at all or only a remarkably reduced content of Neu5Gc) in an efficient concentration using, e.g., large scale bioprocesses.

In a further attempt to reduce the amount of Neu5Gc on glycosylated proteins, the inventor of the present invention allowed the cells (e.g., the CHO cells) used for protein expression to grow in media with limited iron concentrations. It had been shown previously that the activity of the CMP-NeuAc hydroxylase depends on exogenous iron ions. Since iron reduction in media often results in decreased specific growth rates, two additional growth-promoting factors, insulin and glutamine, were tested to determine whether the effect of iron depletion on a decreased Neu5Gc content is due to the limited CMP-NeuAc hydroxylase activity or due to limited growth. Two experimental approaches were used, one with a "one factor at the time" (univariate) approach and the other by using Design-Experts (DOE) software, enabling the recognition of interactions between the aforementioned components. Certainly, the principal focus was on the effect of modified cell culture media on the Neu5Gc content, while growth rate, titre, and the degree of sialylation were also monitored.

Accordingly, the first aspect of the present invention relates to a medium for the cultivation of eukaryotic cells, the medium comprising as (an) additive(s) DMSO, NAcMan, NAcGlc, or any combination of two or more of these additives. The medium comprising the additive(s) may be any medium which is suitable for culturing eukaryotic cells, in particular mammalian host cells. For example, the medium can be an in-house developed (i.e. customised) medium, such as a rich medium adapted and formulated for the cultivation of eukaryotic and in particular mammalian host cells or for use for a particular cell line. The medium may or may not contain serum and/or protein, wherein serum- and protein-free media are preferred. It is understood by those of skill in the art that several cell type- or expression product-adapted cell culture media are conceivable, which all can be supplemented according to the first aspect of the present invention. Alternatively, the medium can be a commercially available standard (basic) medium such as Sigma Ex-CELL®ACF CHO medium, Sigma Ex-CELL®CD CHO 2, 3 medium, Sigma Ex-CELL®CD CHO DHFR: medium, BioWhittaker (Lonza) PowerCHO™1, 2, 3, GS CD medium, BioWhittaker (Lonza) ProCHO™4, 5, AT medium, IrvineScientific CHO™ chemically defined medium, all of which being supplemented with the additives according to the present invention.

In a preferred embodiment, the medium comprises the combination of NAcMan and NAcGlc. Suitable concentrations of NAcMan and NAcGlc are ranging independently upon each other from 3 to 20, from 5 to 10, or from 8 to 10 mM. Preferred combinations of NAcMan and NAcGlc are as follows: 5 to 12 mM NAcMan and 0 to 5 mM NAcGlc. Particularly preferred combinations are >8 or >8.5 mM NAcMan and 1.25-3.75 mM NAcGlc, 6.75-10.25 mM NAcMan and 1.25-3.75 mM NAcGlc, 8.18-10.25 mM NAcMan and 1.25-3.75 mM NAcGlc, and 9.94 mM NAcMan and 3.75 mM NAcGlc.

In another preferred embodiment, the medium additionally comprises $Mn^{2+}$. According to still another preferred embodiment, the medium comprises NAcMan and $Mn^{2+}$, NAcGlc and $Mn^{2+}$, or NAcMan, NAcGlc, and $Mn^{2+}$. The $Mn^{2+}$ concentration may range from 30 to 250, from 50 to 200, from 80 to 180, or from 100 to 150 µM. In a particularly preferred embodiment, the medium comprises NAcMan, NAcGlc, and $Mn^{2+}$, the concentrations of NAcMan and NAcGlc ranging independently upon each other from 3 to 20, from 5 to 10, or from 8 to 10 mM, and the $Mn^{2+}$ concentration being in the range of 30 to 250, 50 to 200, 80 to 180, or 100 to 150 µM. 50, 80, 110, 150, and 180 µM are especially preferred $Mn^{2+}$ concentrations, and 5 to 12 mM and 0 to 5 mM, >8 or >8.5 and 1.25-3.75 mM, 6.75-10.25 and 1.25-3.75 mM, 8.18-10.25 and 1.25-3.75 mM, and 9.94 and 3.75 mM are especially preferred (ranges of) concentrations of NAcMan and NAcGlc, respectively. Particularly desired embodiments are the following combinations in a cell culture medium.

8.75 mM NAcMan, 3.75 mM NAcGlc, and 30 µM $Mn^{2+}$.
8.75 mM NAcMan, 3.75 mM NAcGlc, and 50 µM $Mn^{2+}$,
8.75 mM NAcMan, 3.75 mM NAcGlc, and 80 µM $Mn^{2+}$,
8.75 mM NAcMan, 3.75 mM NAcGlc, and 110 µM $Mn^{2+}$,
8.75 mM NAcMan, 3.75 mM NAcGlc, and 150 µM $Mn^{2+}$,
8.75 mM NAcMan, 3.75 mM NAcGlc, and 180 µM $Mn^{2+}$,
8.75 mM NAcMan, 3.75 mM NAcGlc, and 250 µM $Mn^{2+}$,
10.25 mM NAcMan and 30 µM $Mn^{2+}$, 10.25 mM NAcMan and 50 µM $Mn^{2+}$,
10.25 mM NAcMan and 80 µM $Mn^{2+}$, 10.25 mM NAcMan and 110 µM $Mn^{2+}$,
10.25 mM NAcMan and 150 µM $Mn^{2+}$, 10.25 mM NAcMan and 180 µM $Mn^{2+}$,
10.25 mM NAcMan and 250 µM $Mn^{2+}$,
3.75 mM NAcGlc and 30 µM $Mn^{2+}$, 3.75 mM NAcGlc and 50 µM $Mn^{2+}$,
3.75 mM NAcGlc and 80 µM $Mn^{2+}$, 3.75 mM NAcGlc and 110 µM $Mn^{2+}$,
3.75 mM NAcGlc and 150 µM $Mn^{2+}$, 3.75 mM NAcGlc and 180 µM $Mn^{2+}$,
3.75 mM NAcGlc and 250 µM $Mn^{2+}$.

According to another preferred embodiment, the concentration of DMSO in the medium ranges from 0.25 to 1.5% (w/v). Concentrations of 0.45 to 1.25, 0.65 to 1, and 0.75% (w/v) are particularly preferred.

According to still another preferred embodiment, the iron concentration of the cell culture media was reduced. Whereas standard media utilised for eukaryotic expression systems comprise about 0.2 mM iron, iron concentrations of only 0.05 to 0.1, 0.070 to 0.9, and 0.075 to 0.08 mM are preferred according to that preferred embodiment. A particularly preferred iron concentration is 0.077 mM.

Another (the second) aspect of the present invention relates to a method for producing a glycoprotein, wherein the method comprises the steps of cultivating eukaryotic cells in the medium according to the first aspect and recovering from that medium, or from said cells, the glycoprotein, wherein the glycoprotein exhibits (i) a degree of sialylation that is identical to or higher than the degree of sialylation of the same glycoprotein when produced in the same medium but without the additive(s); and (ii) a content of Neu5Gc that is lower than the content of Neu5Gc of the same glycoprotein when produced in the same medium but without the additive(s).

The eukaryotic cells that can be used in conjunction with the present invention are preferably cells which allow the recombinant expression of a glycoprotein. Exemplary cells are: L cells, C127 cells, Sp2/0 cells, NS-0 cells, NS-1 cells, NIH3T3 cells, PC12 cells, PC12h cells, BHK cells, CHO cells, particularly CHO-SSF, -PD, -HPT1, -DHFR and -K1 cells, COS1 cells, COS3 cells, COS7 cells, CV1 cells, Vero cells, or non-human or non-chicken myeloma cells.

According to a preferred embodiment, the step of cultivating the eukaryotic cells occurs at a temperature of 35 to 38° C. or at about 37° C. A preferred embodiment envisions the eukaryotic cells to be CHO cells and particularly CHO-K1 cells. According to still another preferred embodiment, the medium used in the method for producing a glycoprotein can be any medium which is suitable for cultivating eukaryotic cells, in particular CHO cells, and which can be supplemented with the additives according to the present invention (e.g. Sigma Ex-CELL®ACF CHO medium, Sigma Ex-CELL®CD CHO 2, 3 medium, Sigma Ex-CELL®CD CHO DHFR⁻ medium, BioWhittaker (Lonza) Power-CHO™1, 2, 3, GS CD medium, BioWhittaker (Lonza) ProCHO™4, 5, AT medium, IrvineScientific CHO™ chemically defined medium etc., or any in-house developed, customised medium). According to still another preferred embodiment, the method further comprises, prior to the step of cultivating the eukaryotic cells in the medium including the additives, the step of cultivating the eukaryotic cells in the same medium but without the additives and, optionally also without $Mn^{2+}$.

As mentioned in the foregoing, the glycoproteins produced using the methods and media according to the present invention may be any type of glycoprotein (in particular a glycoprotein having an elevated Neu5Gc level), including a recombinant glycoprotein, a therapeutic glycoprotein, or fragments thereof. It may be a single-chain (monomeric) glycoprotein or a multi-chain (homo- or hetero-multimeric) glycoprotein. The glycoproteins are preferentially secreted proteins. A preferred single-chain (monomeric) glycoprotein is a cytokine or a hormone. A preferred multi-chain glycoprotein is a monoclonal antibody, a particularly preferred multi-chain glycoprotein is a monoclonal antibody in the IgG format.

As also mentioned in the foregoing, the iron concentration of the media utilised for the method of the second aspect of the present invention is preferably 0.05 to 0.1, 0.070 to 0.9, or 0.075 to 0.08 mM, with an iron concentration of 0.077 mM being most preferred.

A further (the third) aspect of the present invention is the use of a medium comprising DMSO, NAcMan, NAcGlc, or any combination thereof, as additive(s) for controlling the sialic acid content of a glycoprotein produced by a eukaryotic cell, wherein the glycoprotein exhibits (i) a degree of sialylation that is identical to or higher than the degree of sialylation of the same glycoprotein when produced in the same medium but without the additive(s); and (ii) a content of Neu5Gc that is lower than the content of Neu5Gc of the same glycoprotein when produced in the same medium but without the additive(s).

Another (the fourth) aspect of the present invention is the use of DMSO, NAcMan, NAcGlc, or any combination thereof, as additive(s) in a medium for eukaryotic cells for producing a glycoprotein, wherein the glycoprotein exhibits (i) a degree of sialylation that is identical to or higher than the degree of sialylation of the same glycoprotein when produced in the same medium but without the additive(s); and (ii) a content of Neu5Gc that is lower than the content of Neu5Gc of the same glycoprotein when produced in the same medium but without the additive(s).

The last (the fifth) aspect of the present invention relates to a glycoprotein producible by the method according to the second aspect of the invention, wherein the glycoprotein exhibits (i) a degree of sialylation that is identical to or higher than the degree of sialylation of the same glycoprotein when produced in the same medium but without the additive(s); and (ii) a content of Neu5Gc that is lower than the content of Neu5Gc of the same glycoprotein when produced in the same medium but without the additive(s).

In a preferred embodiment of this aspect, the glycoprotein exhibits a degree of sialylation increased by at least about 5%, preferably by at least about 10%, 15%, 20%, 25% or 30%, and a decrease of the Neu5Gc content by at least about 50%, preferably by at least about 60% 70%, 80%, 90%, or 99%, when compared with the degree of sialylation and Neu5Gc content, respectively, of the same glycoprotein when produced in the same medium but without the additive(s).

The percentage of sialic acid in relation to all sugar residues on the protein was additionally calculated by measuring the amount of three groups of isoforms: (i) isoforms 1, 2, and 3; (ii) isoforms 4, 5, and 6; and (iii) isoforms 7 and 8. Since group (i) comprises the more basic isoforms, their percentage was multiplied by 2, the group (ii) percentage was multiplied by 5, and the last group (iii) was multiplied by 7. Subsequently, the inventor compared the degree of sialylation of her own products, either obtained from culture medium including the additive(s) or obtained from culture medium without the additive(s), to that of the originator product (for the purpose of this calculation, the originator product was set to 100% sialylation). Interestingly, in most cases an increase of the degree of sialylation relative to the originator's product was detected when culture medium including the additive(s) had been utilised. As the respective figure obtained by calculating the originator's product degree of sialylation was set to 100, it was clear that a larger figure is tantamount to an increase by x %. Typical increases obtained by the inventor were 5%, 10%, 15%, 20%, 25%, or even 30%.

The term "additive" as used herein throughout the description and the claims is limited to DMSO, NAcMan, NAcGlc, and combinations thereof. In particular, $Mn^{2+}$, other inorganic or organic salts, other carbohydrates, and buffers, as they are frequently utilised in culture media for eukaryotic cells are not additives according to the nomenclature herein but are termed ingredients or components.

BRIEF DESCRIPTION OF THE DRAWINGS

FIG. 4a is a graphical comparison between growth curves in batch processes run with standard media and with media comprising 0.75% DMSO (w/v).

FIG. 4b depicts a graph showing the glucose and glutamine consumption and the lactate and $NH_4^+$ production in a batch process run with standard media. Glc means glucose, Gln is glutamine, Lac is lactate, and NH4 is ammonia/the ammonium ion.

FIG. 11a and FIG. 11b depict the comparison for the sialylation profile (a) and Neu5Gc content (b) in non-modified (grey) and modified (black) medium when performing shaking in a shaking incubator at 90 rpm and 150 rpm, respectively (for details see Example 7 below).

DETAILED DESCRIPTION OF THE ILLUSTRATIVE EMBODIMENTS

Figure 1A:
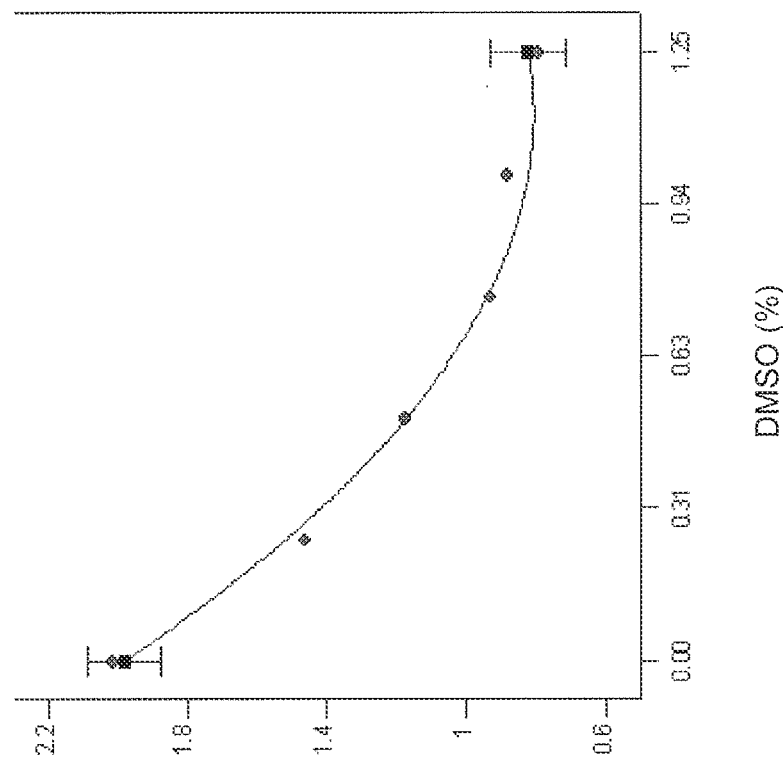
FIG. 1a and FIG. 1b each depict a graph showing the impact of DMSO in a concentration range from 0% to 1.25% (w/v) on the percentage of the most acidic isoforms 7 and 8 (a) reflecting the degree of sialylation of the glycoprotein tested and on the content of Neu5Gc (b).

The present inventor conducted a series of experiments to test the optimum conditions to cultivate a large number of different eukaryotic cells. The outcome was that the parameters modified by the inventor (concentration of the additive(s) in the medium, time of addition of the additives to the medium, temperature, ionic strength, and pH of the medium) had almost the same impact on the fermentation process, regardless which type of cells had been used as the host cells.

For example, the present inventor found that the relative content (%, w/w) of the most acidic isoforms of the glycoproteins tested reflecting the overall degree of sialylation in the glycoproteins was always higher after a cell cultivation process at 37° C. than after a cell cultivation process at 33° C. The inventor identified 35° C. as the minimum temperature to allow for a significantly increased percentage of the most acidic isoforms reflecting the degree of sialylation, although even at 33° C. a small increase of the percentage of the most acidic isoforms was observed. Exactly the same results were obtained in regard of the amount of Neu5Gc and its reduction.

As demonstrated in greater detail in the examples below, the optimum concentration of the additives ranges from about 0.7 to 0.8 and is frequently 0.75% (w/v) for DMSO, ranges from 5 to 12, 6.75 to 10.25, or is frequently 8.75 or 9.94 mM for NAcMan, and ranges from 0 to 5, 1.25 to 3.75, or is frequently 3.75 mM for NAcGlc, preferably in the presence of $Mn^{2+}$ having a concentration of 30 to 250 µM in case of the addition of at least one of NAcMan and NAcGlc. In order to determine the optimum concentration of the additives, various parameters were scrutinised and taken into account: cell growth, cell viability, yield of the glycoprotein, content of Neu5Gc, and degree of sialylation.

Thus, an about 50% to 60% reduction of the content of Neu5Gc could be accomplished (e.g., the content of Neu5Gc decreased from about 1.8 to about 0.8% in case of darbepoetin alfa using a shake flask batch process, and from about 1.8 to about 1% when using a bioreactor batch process) when DMSO was added in a concentration of 0.75% (w/v). Simultaneously, the percentage of the most acidic isoforms (reflecting the increased degree in sialylation) could be increased by about 25 to 45% (e.g., from about 1.0 to about 1.35% when using a shake flask batch process, and from about 1.8% to about 2.2% when using a bioreactor batch process) when DMSO was added in a concentration of 0.75% (w/v). The addition of DMSO took place in rich in-house standard media at the beginning of the culturing.

Similarly, the concentration of 5.0 mM each of NAcGlc and NAcMan brought about a level of the most acidic isoforms (being an indicator for the increased degree of sialylation) in, e.g., darbepoetin alfa that was increased from about 0.2% to about 2% using a shake flask batch process. Concomitantly, the Neu5Gc content was significantly decreased from about 1.8% to about 0.5%. Similar results were obtained when the concentration of NAcMan was about 5.0 mM and the concentration of NAcGlc was only 3.75 mM. Thus, there is no need to exceed a concentration of 3.75 mM for NAcGlc, although it is not harmful at all. Slightly better results are obtainable by employing the above concentrations of NAcGlc and NAcMan, but to add to the media, as another supplement, $Mn^{2+}$ in the concentration ranges presented above.

Figure 6:
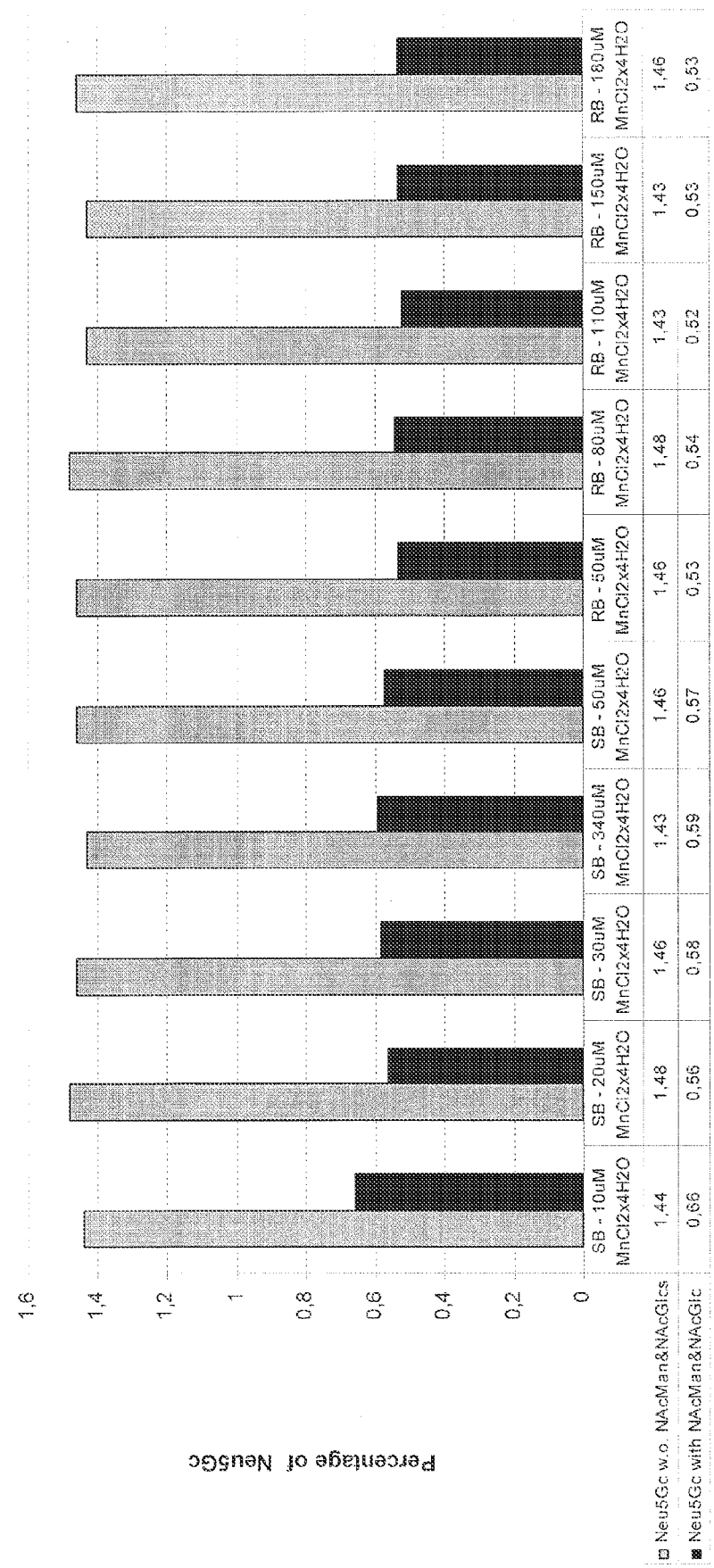
FIG. 6 depicts a graph showing the Neu5Gc content in glycoproteins produced by cells cultivated using two types of bioprocesses (SB, RB, both performed with in-house media customised for CHO cells; see above) wherein the media comprised $Mn^{2+}$ (50, 80, 110, 150, and 180 µM each) in the presence (black columns) and in the absence (grey columns) of NAcMan and NAcGlc (8.75 mM each, if present). Abbreviations: SB=simple batch; RB=repeated batch.

In addition, the concentration of 8.75 mM each of NAcGlc and NAcMan (tested initially, before the inventor had identified 3.75 mM NAcGlc to be the threshold concentration, beyond of which no further significant improvement is obtained) in the presence of various $Mn^{2+}$ concentrations (ranging from 50 to 180 µM) brought about a Neu5Gc content reduction from about 1.4 or 1.5% to values in the range of 0.5 to 0.7% (e.g., 0.52, 0.53, 0.54, 0.56, 0.58, 0.66%) for darbepoetin alfa using a simple batch or repeated batch process performed in a shake flasks system (see FIG. 6). For further preferred concentrations of NAcGlc and NAcMan the skilled reader is referred to Tables 2 and 3 and FIGS. 7 to 9.

The experiments described in the following examples have been performed with six glycoproteins, in the context of Examples 1 to 6 termed "glycoproteins" or "human glycoproteins". In particular, three human cytokines and three monoclonal antibodies were used. Unless explicitly indicated differently, the numerical data presented above and hereinafter have been collected by using one of the cytokines (i.e., darbepoetin alfa) as an exemplary protein. The results obtained with the other five proteins are very much comparable with the data depicted in the present application and corroborate the results obtained with darbepoetin alfa.

Example 1

General Experimental Setting

Recombinant CHO cells expressing high titres of the glycosylated human glycoproteins were cultivated in suspension culture using rich in-house standard medium without additives according to the invention. After 2 weeks of passages, the cells were first harvested and subsequently inoculated into the same medium, however, supplemented with a range of DMSO concentrations from 0.25% to 1.50% (w/v). The effect of DMSO on growth, productivity, degree of sialylation, and Neu5Gc content was studied.

"One factor at the time"-experiments with different DMSO concentrations at 37° C. and 33° C., respectively, were performed at first in an attempt to determine the DMSO concentration and temperature which are best to minimise the Neu5Gc content on the glycoproteins secreted. To study the interaction between the parameters (i) DMSO concentration, (ii) time of DMSO addition, and (iii) time of the temperature shift (from 37° C. to 33° C.), further experiments were performed with the Design-Expert/Design-Ease programme (Stat-Ease, Inc., Minneapolis, Minn., USA) using the response surface method. Parameters (i), (ii), and (iii) were chosen as numeric factors and the axial points were set slightly out of already known ranges in order to cover a wide design space. One replicate on axial points, one replicate on factorial points and 4 centre points were performed. The results were analysed using the Design of Expert (DOE) software (Design-Expert, Version 7.1). The results of the shake flask experiments were confirmed in the Biostat®B bioreactor (Sartorius, B. Braun Biotech International, Germany). Exponentially growing cells were taken from cell culture flasks having a surface area of 225 $cm^2$ (Corning®Costar®). A Biostat®B bioreactor with a working volume of 5 litres was inoculated with $2 \times 10^5$ cells/ml. Cells were cultivated in a batch mode under standard conditions (37° C., pH 7.0, dissolved oxygen concentration (DOT) 50%) in the rich in-house standard medium supplemented with 0.75% (w/v) DMSO.

In order to study the effect of key intermediates of the metabolic pathway leading to the sialylation of the glycoproteins and consequently to the conversion of Neu5Ac to Neu5Gc, a two factorial minimal resolution IV design, which allows for the estimation of the main effects, was established. Said design allowed the determination which of the components NAcMan, NAcGlc, Man, Fru, and Gal has/have an impact on the degree of sialylation and conversion of Neu5Ac to Neu5Gc. To confirm the results from the DOE findings, the production medium was enriched with 8.75 mM NAcMan and 8.75 mM NAcGlc in combination with manganese ($Mn^{2+}$) salts in different concentrations, e.g., in the concentrations mentioned earlier in this application.

Cell viability was determined by the trypan blue exclusion method. The cell concentration was determined using a Vi-CELL™ Series Cell Viability Analyzer (Beckman Coulter, Fullerton, Calif., USA). Glucose, lactate, glutamine, and ammonia ($NH_4^+$) concentrations were measured during the growth phase using a BioProfile Analyzer for mammalian cell culture (BioProfile 100 plus, Nova Biomedical, Waltham, USA). Additionally, oxygen and carboxyl oxygen concentrations were monitored daily using pHOx (Stat Prophile pHOx Basic, Nova Biomedical, Waltham, USA). Secreted glycoprotein concentrations were quantified by enzyme linked immunosorbent assay (ELISA), and the titres were expressed in µg/ml.

Example 2

Determination of the Concentration of the Secreted Glycoproteins

The concentration of the secreted glycoproteins was quantified using an enzyme linked immunosorbent assay kit from R&D Systems (R&D Systems, Inc., Minneapolis, Minn., USA) according to the manufacturer's instructions. Microplate wells, pre-coated with monoclonal (mouse) antibodies specific for the respective glycoproteins expressed were first incubated with standard blank samples and specimens. After removal of excess solution, the wells were incubated with anti-glycoprotein polyclonal antibodies conjugated to HRP (horseradish peroxidase). During the second incubation, the complexes formed between antibody-enzyme conjugates and the immobilised glycoproteins and the excess conjugates were removed by washing, followed by the addition of a chromogen. Oxidation by HRP resulted in a coloured complex (blue). The reaction was stopped by the addition of acid, which causes a change of the colour from blue to yellow. The absorbance of the coloured solution was measured photometrically at 450 nm (Micro plate reader, Tecan, Columbus, USA) and was proportional to the concentration of the glycoprotein in the sample.

Example 3

Purification of the Secreted Glycoproteins

At the end of the batch culture the cells were removed. The glycoproteins were purified from the remaining harvests by means of immuno-affinity chromatography. Briefly, up to 2 mg of each of the glycoproteins per ml of the chromatographic resin (20-500 ml of the harvest) were loaded onto the column. Elution of the glycoproteins was performed with 0.1 M Na-phosphate buffer, pH 2.5. By adding 1 M Na-phosphate buffer, pH 7.5 (made up by a combination of $Na_2H$-phosphate and $NaH_2$-phosphate), the pH of the eluate was immediately adjusted to 7 and then stored for further analysis at below −60° C.

For determining the glycoprotein concentration in purified samples, RP-HPLC was used. Chromatographic separation of the respective glycoprotein from other (contaminating) components was based on the differences in their hydrophobicity, and the glycoprotein concentration of the samples analysed was determined by comparing the response obtained with the sample solution to the response obtained with a calibration standard solution.

Example 4

Isoform Distribution and Differentiation of Sialic Acids

Following glycoprotein purification, the isoform distribution of the immuno-affinity purified glycoproteins was determined by anion exchange chromatography (AEX). The chromatographic separation of various isoforms is based on the differences in their charges. Basic (less sialylated) isoforms elute from the column earlier than the more acidic (more sialylated) ones.

Sialic acids (Neu5Gc, Neu5Ac, Neu-5,7Ac2, Neu5Gc9Ac, Neu-5,9Ac2, Neu-5,8,9Ac3) were differentiated using highly sensitive RP-HPLC. Enzymatic desialylation with neuraminidase (a2-3,6,8,9-neuraminidase (Sialidase) from *Arthrobacter ureafaciens*, Roche, USA) released sialic acids. The released sialic acids were labelled with the fluorescent dye 1,2-diamino-4,5-methylenedioxybenzene (DMB). DMB-labelling is non-selective and therefore provides a pool of labelled sialic acid derivates in stoichiometric amounts. Derivates of the DMB-labelled sialic acids were separated on an RP-HPLC column using isocratic elution. Fluorescence detection was performed at an excitation wavelength of 373 nm and an emission wavelength of 448 nm.

Figure 1B:
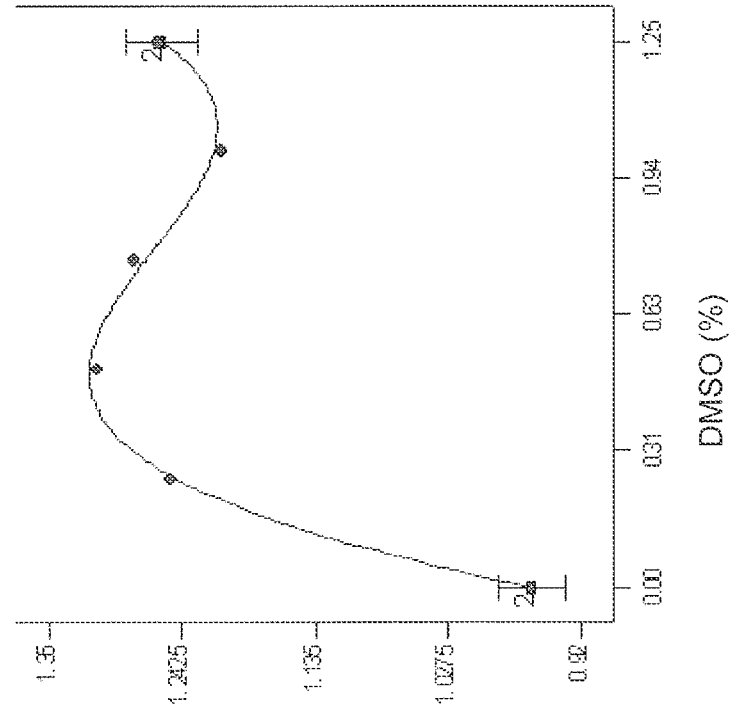

In a first experiment, the inventor compared the effect of DMSO in the cell culture medium on viability, productivity, degree of sialylation, and Neu5Gc content when growing the cells at 37° C. and 33° C. A significant decrease of the Neu5Gc content was observed for all glycoproteins with DMSO in the cell culture medium. A decrease of about 50 to 60% (e.g., from about 2% to about 0.9% in case of darbepoetin alfa, see FIG. 1b) was achieved with the addition of 0.75% (w/v) DMSO. In detail, FIG. 1b depicts an average Neu5Gc content for all glycoproteins tested of 2.01% in media without DMSO, and the average Neu5Gc content dropped to 1.46%, 1.17%, 0.93%, 0.88%, and 0.79% by supplementing the media with 0.25%, 0.5%, 0.75%, 1%, and 1.25% DMSO, respectively.

The average content of the most acidic isoforms obtained with all glycoproteins tested runs from 0.96% to 1.31%. It means that in media without DMSO the average figure was 0.96%. By supplementing the media with DMSO to final concentrations of 0.5%, 0.75%, 1%, or 1.25%, the average figures for the most acidic isoforms were increased to 1.31%, 1.28%, 1.21%, and 1.26%, respectively.

By comparing the profiles of cell growth, viability, production, and sialylation pattern, the optimal DMSO concentration chosen turned out to be in the range of 0.6 to 0.8%, 0.75% being regularly (for most of the glycoproteins tested) preferred. This correlates quite well with the optimal DMSO concentration in terms of Neu5Gc content and content of the most acidic isoforms (see below).

Initially, the inventor avoided the addition of DMSO to the cell culture at the beginning of the bioprocess, because she speculated that such addition might not be optimal, since the cells had no time for an optimal lag phase-growth (adaptation). In order to confirm that speculation, further experiments using DOE software were performed to analyse the interaction between the following parameters: (i) DMSO concentration, (ii) time of DMSO addition, and (iii) time of the temperature shift (from 37° C. to 33° C.). A full factorial central composite design, where two factorial parameters (i) and (ii) were varied over five levels, (i) 0.0% to 0.5% (w/v) and (ii) 0 h to 72 h, and one categorical factor (iii) was varied over 2 levels, 37° C. to 33° C., was performed. Four central points were included and the DOE programme was used. Batch cultures were grown over a period of 8 days. Viable cell density and viability of the cells were measured in the middle and at the end of that period. The final titre (concentration of each glycoprotein in the culture medium) was measured in the supernatants with ELISA. The respective glycoproteins were purified from the remaining harvests. The content of Neu5Gc on the purified glycoproteins was determined, and the acidic isoform distribution reflecting the degree of sialylation was measured with AEX. From the growth perspective, no significant model was found, but growth was not inhibited in any tested conditions, and final cell viability was above 97.5% in all cases of (i), (ii), and (iii) tested.

A linear model was suggested for the titre, and only parameters (i) and (iii) were chosen as significant model terms. By the addition of DMSO the titres were slightly decreased, on average by about 5 to 10% (e.g., from approximately 61 µg/ml to 57 µg/ml in case of darbepoetin alfa), regardless whether the temperature was 37° C. or 33° C.

Figure 2A:
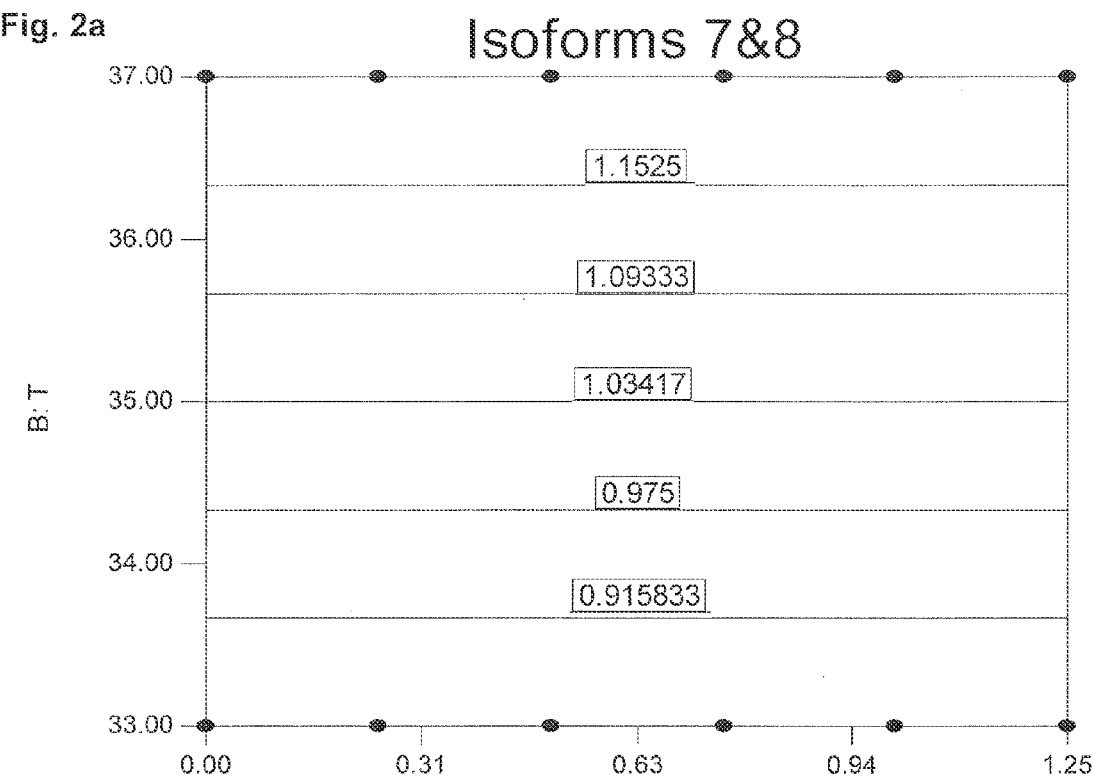
FIG. 2a and FIG. 2b depict contour diagrams created by the DOE software presenting the impact of DMSO addition in a concentration range from 0% to 1.25% (w/v) on the percentage of the most acidic isoforms 7 and 8 (a) reflecting the degree of sialylation and on the Neu5Gc content on the secreted glycosylated protein (b). In both diagrams, time of DMSO addition (ii) and time of temperature shift (iii) were excluded from the model (see also Examples 1 and 4).

For the content of the most acidic isoforms, a linear model was suggested, and only the temperature was selected as a significant model term. A lower temperature resulted in a lower content of the most acidic isoforms (FIG. 2a).

Figure 2B:
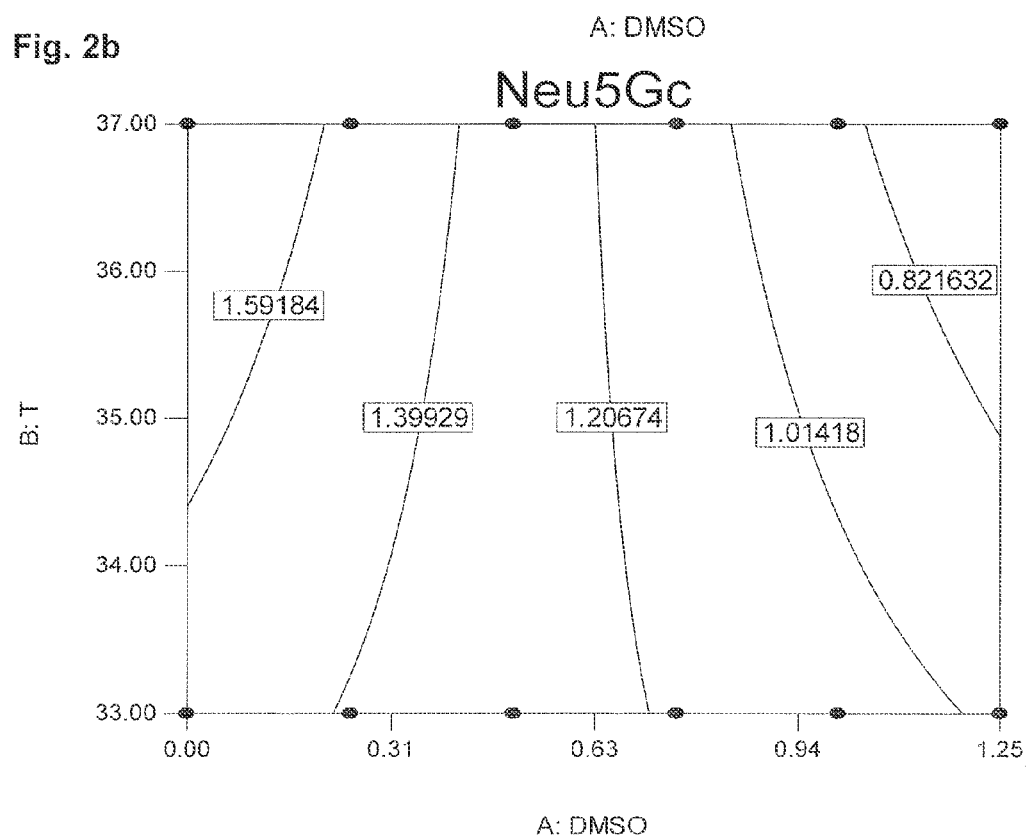

A two-factorial model was suggested for the Neu5Gc content, and the time of DMSO addition was excluded from the model. The addition of DMSO resulted in a decreased Neu5Gc content, and the inhibitory effect of DMSO was more evident in bioprocesses running at 37° C. the whole time than in bioprocesses with a shift to 33° C. The optimal concentration of DMSO at the beginning of the batch culture running at 37° C. was determined to be 0.6-0.8%, and specifically about 0.75% in many cases (FIG. 2b; see also above the optimal DMSO concentration in terms of cell growth, viability, production, and sialylation pattern). In detail, FIG. 2b shows that 1.25% is the optimal DMSO concentration, if the Neu5Gc content alone is considered. FIG. 2a also shows that the content of isoforms 7 and 8 at a given DMSO concentration is dependent only upon the temperature if the content of the most acidic isoforms is at issue. The DOE calculated that a 0.75% DMSO concentration is optimal in terms of the highest content of acidic isoforms and the lowest content of Neu5Gc. Thus, the inventor's suspicion that the addition of DMSO to the cells at the onset of the cultivation process might be harmful could be invalidated by the DOE experiment described above.

Figure 3:
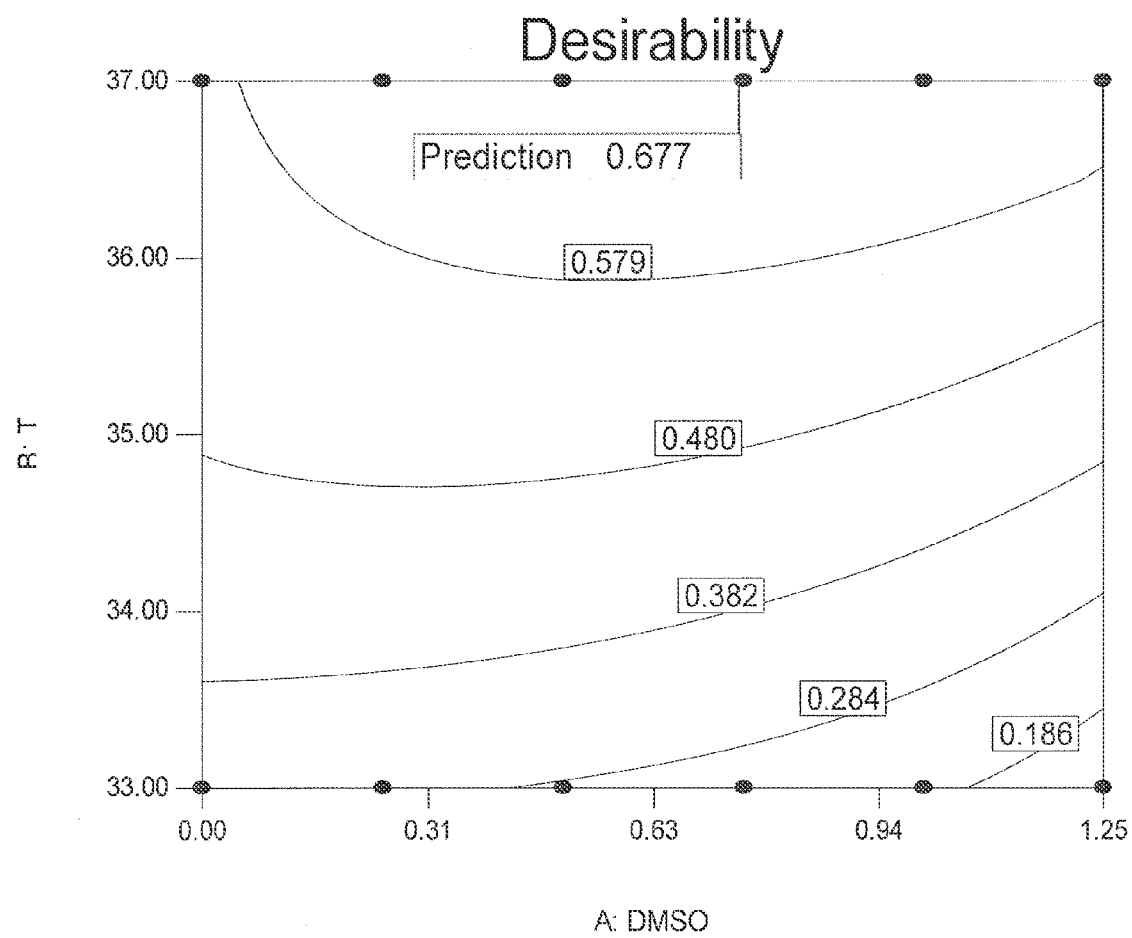
FIG. 3 depicts a desirability diagram created by the DOE software presenting ranges of desirability to achieve a minimal Neu5Gc content by using an optimal DMSO concentration and temperature. Table 1 shows the respective numerical values of the calculated confidence interval (CI) and predicted intervals (PI) for titre, specific productivity, specific growth rate, percentage of isoforms 7 and 8, and percentage of Neu5Gc.

According to the optimal range of the DMSO concentration, a numerical and graphical optimisation was performed using DOE software (FIG. 3). A minimal content of Neu5Gc and a maximal content of the most acidic isoforms were chosen as very important parameters, while increased titres and growth rates were weighted as medium important parameters. The ramps were extended a little over the limits. Table 1 shows the respective numerical values of the calculated confidence intervals (CI) and predicted intervals (PI) for titre, specific productivity, specific growth rate, content of the most acidic isoforms, and content of Neu5Gc. The specific productivity (Qp) was calculated following Equation 1 and expressed as pg of glycoprotein/cell/day (pcd).

$$Qp = (P2-P1)/((X2+X1)*(t2-t1)/2) \quad \text{Equation 1}$$

(P2 and P1 are concentrations of secreted glycoprotein at the end and at the beginning of the repeated batches, respectively; X1 and X2 are cell concentrations at the corresponding time points t1 and t2).

The specific growth rate was calculated following Equation 2 and represents the overall biomass accumulation under the growth curve from the beginning to the end of the batch process (expressed as a logarithmic value per day ($day^{-1}$)).

$$\text{Specific growth rate} = \ln(X2/X1)/(t2-t1) \quad \text{Equation 2}$$

(X1 is the number of viable cells on day 0 and X2 the number of cells at the end of the repeated batches, respectively. t1 is time 0, and t2 is time 7 or the end day of the process, respectively.)

The point prediction function of the DOE software calculated with 0.677 desirability that by using 0.75% (w/v) DMSO as the most desirable concentration at the beginning of the batch culture and maintaining the cultivation at 37° C. the content of Neu5Gc will be no more than 1.09%±0.14%. The confidence intervals (CI) show that, when the process is performed using the described settings, there is a 95% chance that the Neu5Gc content will be in the range of 0.95% to 1.23% and the content of the most acidic isoforms will be in the range of 1.07 to 1.35%. In general, the CI shows what the result is highly likely to be while only one experiment for each glycoprotein is performed as a confirmation test.

In the culture medium analysed (rich in-house medium supplemented with DMSO), the titres, growth rates, and degree of sialylation will not be decreased relative to the same medium with no DMSO supplementation.

TABLE 1

Numerical analysis using the point prediction function of the DOE software

| Factor | Name | Level | Low Level | High Level |
|---|---|---|---|---|
| A | DMSO | 0.75 | 0 | 1.25 |
| B | Temperature | 37 | 33 | 37 |

| Response | Prediction | 95% CI low | 95% CI high | 95% PI low | 95% PI high |
|---|---|---|---|---|---|
| Titre (µg/ml) | 65.56 | 56.26 | 77.38 | 45.03 | 104.17 |
| Specific productivity (pcd) | 2.43 | 2.02 | 2.98 | 1.55 | 4.33 |
| Specific growth rate ($day^{-1}$) | 0.54 | 0.51 | 0.58 | 0.45 | 0.64 |
| Isoforms 7&8 (%) | 1.21 | 1.07 | 1.35 | 0.85 | 1.58 |
| Neu5Gc (%) | 1.09 | 0.95 | 1.23 | 0.73 | 1.45 |

Thus, FIG. 3 is a desirability plot, which represents only the desirability to get lower Neu5Gc contents and higher degrees of sialylation (higher contents of the most acidic isoforms) for one of the glycoproteins. To get the numbers, one must look into the point prediction function of the DOE software, which tells that by using 0.75% DMSO the Neu5Gc will be within the prediction interval (PI) 0.73 and 1.45% and the content of the most acidic isoforms within the prediction interval (PI) 0.85 and 1.58. Table 1 displays these figures.

Figure 4C:
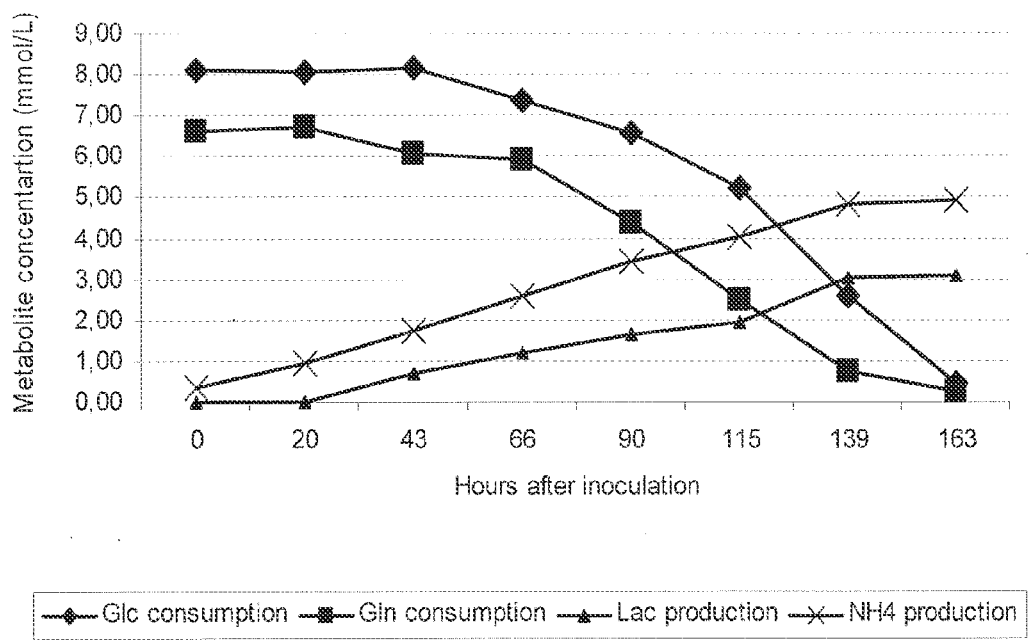
FIG. 4c depicts a graph showing the glucose and glutamine consumption and the lactate and $NH_4^+$ production in a batch process run with standard media comprising DMSO. Again, Glc is glucose, Gln is glutamine, Lac is lactate, and NH4 is ammonia/the ammonium ion.
Figure 4D:
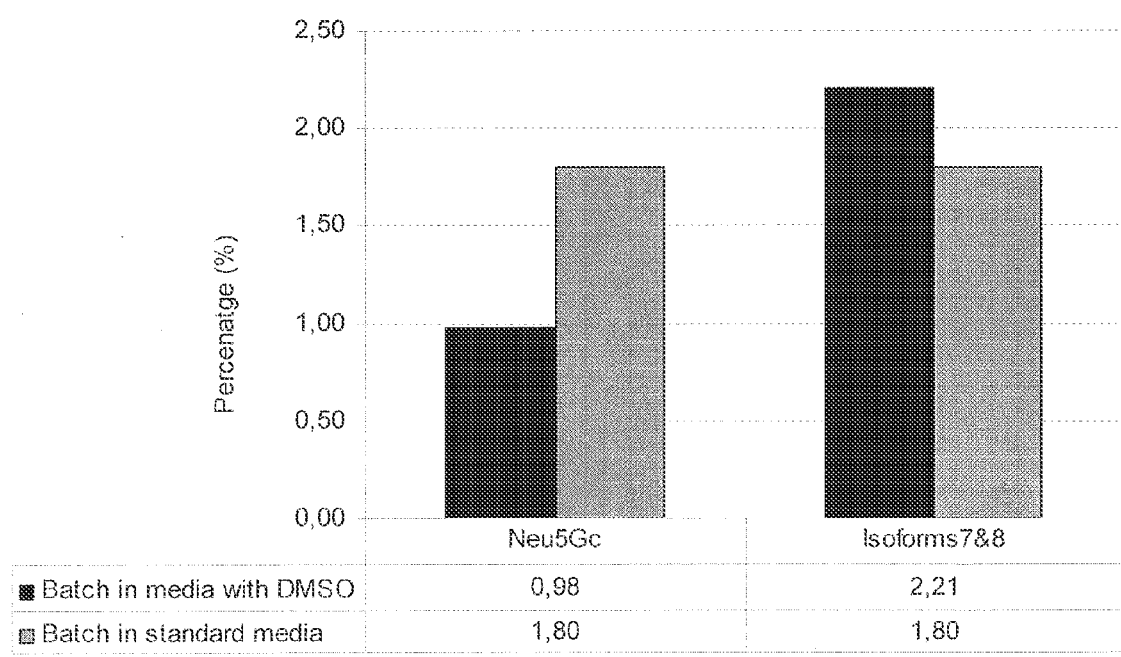
FIG. 4d depicts the improvements regarding the content of isoforms 7 and 8 and of Neu5Gc in a 5 L-batch bioreactor with standard media comprising DMSO vs. the same standard media comprising no DMSO.

Confirmation experiments were performed in the Biostat® B bioreactor with a working volume of 5 litres at an initial cell density of $2\times10^5$ cells/ml. The growth behaviour of the cells in the presence of DMSO was comparable to that in the absence of DMSO. No effect of DMSO on metabolism, aeration, or productivity was detected (FIGS. 4a-4c). The content of Neu5Gc was lowered by about 50-60% (e.g., to about 1%) compared to about 1.8% in the batch process without DMSO, confirming the observations made in shake flask cultures. Additionally, the content of the most acidic isoforms increased from about 1.8% to about 2.2% (FIG. 4d).

Example 5

Medium Supplementation with NAcMan and NAcGlc

In further supplementation experiments using the key intermediates of the metabolic pathway leading to the sialylation of glycoproteins, none of the tested medium additives (NAcMan, NAcGlc) and none of the additional medium components (Man, Fru, Gal) were detected to significantly effect growth rates, titres, or productivities.

Figure 5A:
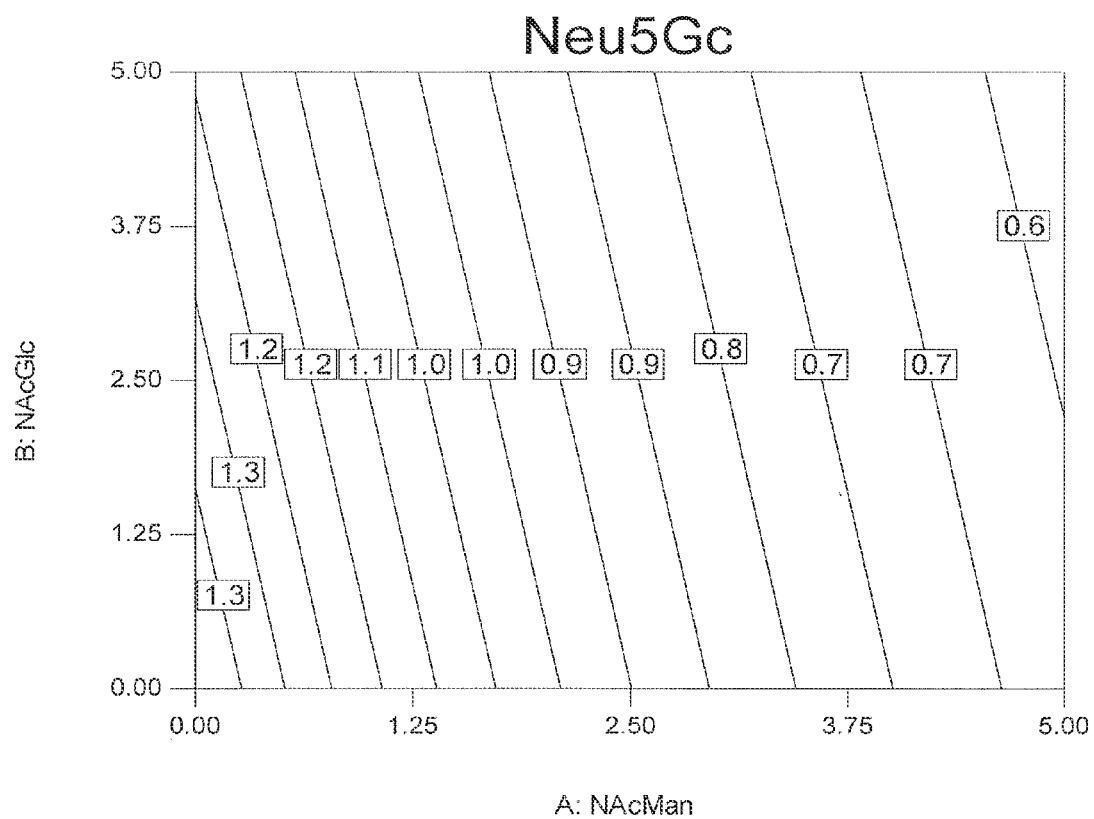
FIG. 5a depicts a contour diagram showing the effect of NAcMan and NAcGlc (the additives) on the Neu5Gc content. The X and Y axes of the graph represent the concentration range (0 to 5 mM) of NAcMan and NAcGlc, respectively, although only two concentrations (0 mM, 5 mM, for each of the additives) were tested in that experiment. When using a medium without the additives, the Neu5Gc content was measured to be 1.3%. However, when media with 5 mM NAcMan and/or 5 mM NAcGlc were employed, the Neu5Gc content was down to only 0.7 or even 0.6%. To this end, MinResIV design (a subalgorithm of DOE software) was used. The DOE programme subsequently calculates the effect of the additives. It indicates that the effect of reducing the Neu5Gc content is more pronounced, if the concentration of NAcMan and NAcGlc is increased, which is perfect support and confirmation for the result obtained experimentally. In the graph, the contents of Neu5Gc (%), either measured experimentally or calculated by DOE, are given in white boxes.
Figure 5B:
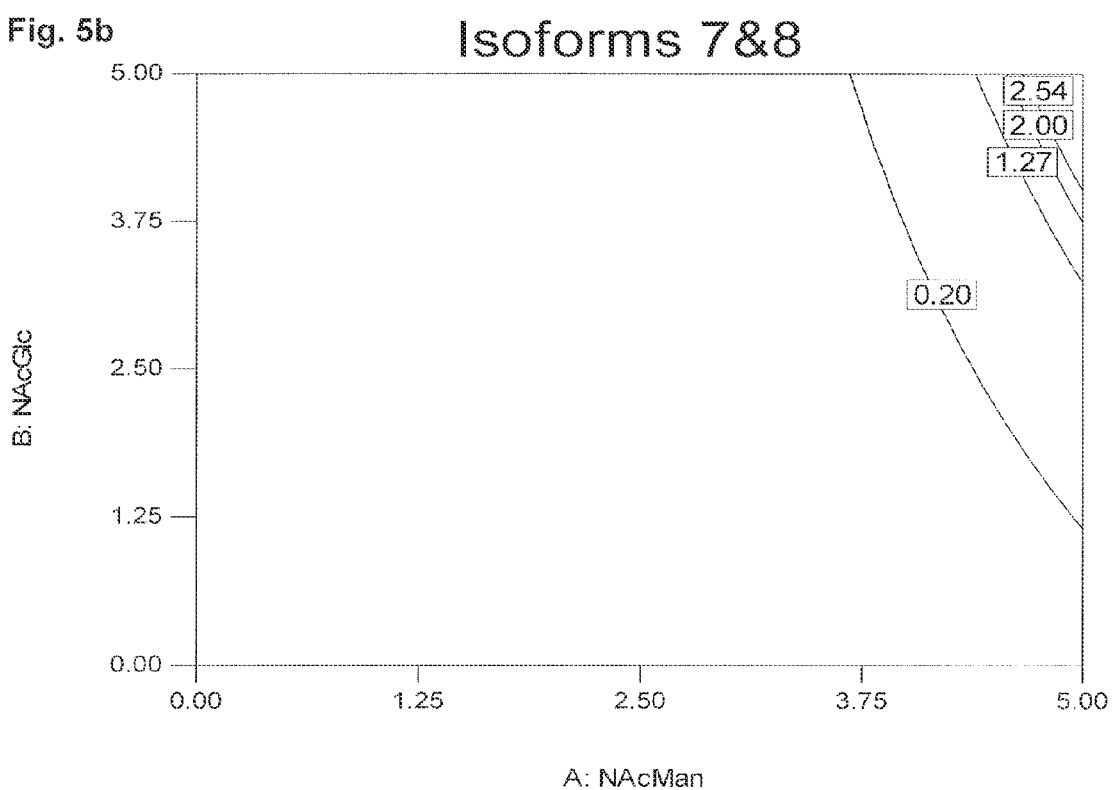
FIG. 5b depicts a contour diagram showing the effect of NAcMan and NAcGlc (the additives) on the content (%) of the most acidic isoforms (isoforms 7 and 8) reflecting the overall degree of sialylation, as described previously. The X and Y axes of the graph represent the concentration range (0 to 5 mM) of NAcMan and NAcGlc, respectively, although again only two concentrations (0 mM, 5 mM, for each of the additives) were tested in that experiment. When using a medium without the additives, the content of isoforms 7 and 8 was measured to be as low as 0.2%. However, when media with 5 mM NAcMan and/or 5 mM NAcGlc were employed, the content of isoforms 7 and 8 was significantly increased, i.e., to 2%. Again, MinResIV design (a subalgorithm of DOE software) was used. The DOE programme calculated the effect of the additives on the content of isoforms 7 and 8. As expected, the content of isoforms 7 and 8 increases with increasing concentrations of the additives. In the graph, the contents of isoforms 7 and 8(%) are given in white boxes.

However, concerning the Neu5Gc content of the glycoproteins, NAcMan and NAcGlc, either alone or in combination, were surprisingly detected to significantly affect, i.e., decrease the content of Neu5Gc (FIG. 5a shows that NAcMan and NAcGlc independently affect the Neu5Gc content, wherein NAcMan has a major effect and NAcGlc shows an additional effect). By increasing for example the NAcMan content in the fermentation medium to 5 mM, the content of Neu5Gc could be lowered (e.g., to as low as about 0.5% in case of darbepoetin alfa). In addition, NAcMan and NAcGlc were found to have a positive effect on the content of the most acidic isoforms (FIG. 5b).

In the optimisation procedure using the DOE programme, a decreased Neu5Gc content and an increased content of the most acidic isoforms were chosen as important parameters, and the programme calculated with a desirability of 0.626 that by introducing NAcGlc and NAcMan into the medium at a concentration of 5 mM, the Neu5Gc content will be reduced by at least 30 to 50% (e.g., to a value ranging from 0.5% to 0.7%).

Based on these results, further confirmation experiments were performed, wherein a medium with different manganese concentrations (e.g., the concentrations mentioned earlier in this application) was supplemented with 8.75 mM NAcMan and 8.75 mM NAcGlc. Simple batch and repeated batch experiments in shake flasks were performed. In all tested combinations, an average decrease of the Neu5Gc content on the final protein product by 50 to 75% (e.g., from about 1.45% to about 0.56% in case of darbepoetin alfa) was detected (FIG. 6) confirming the DOE optimisation procedure results.

Example 6

In another set of experiments, the inventor initially tested the impact of media including 8.75 mM NAcMan and 8.75 mM NAcGlc (later on, the inventor recognised that a combination of 5 mM to 12 mM NAcMan and 0 mM to 5 mM NAcGlc were more appropriate concentrations) with different manganese concentrations (e.g., using the concentrations mentioned earlier in this application). Whatever the manganese concentration was, the Neu5Gc content was decreased from about 1.0% to about 0.5%. Therefore, the inventor established DOE experiments and determined the influence of different concentrations of NAcMan and NAcGlc on the Neu5Gc content. Since an increased degree of sialylation is likewise an important parameter, the content of the most acidic isoforms was also measured. Design expert response surface model was created with two numerical factors, NAcMan concentrations ranging from 5 mM to 12 mM and NAcGlc concentrations ranging from 0 mM to 5 mM. 10-day repeated batch processes were established, with initially multiplying the cells to 20×10$^6$/ml in medium without supplements and then exchanging the un-supplemented medium with supplemented medium. Glycoproteins were isolated only from supplemented media. Titre, Neu5Gc content, and the content of the most acidic isoforms were measured. The specific productivity (Qp) was calculated as described above.

Figure 7:
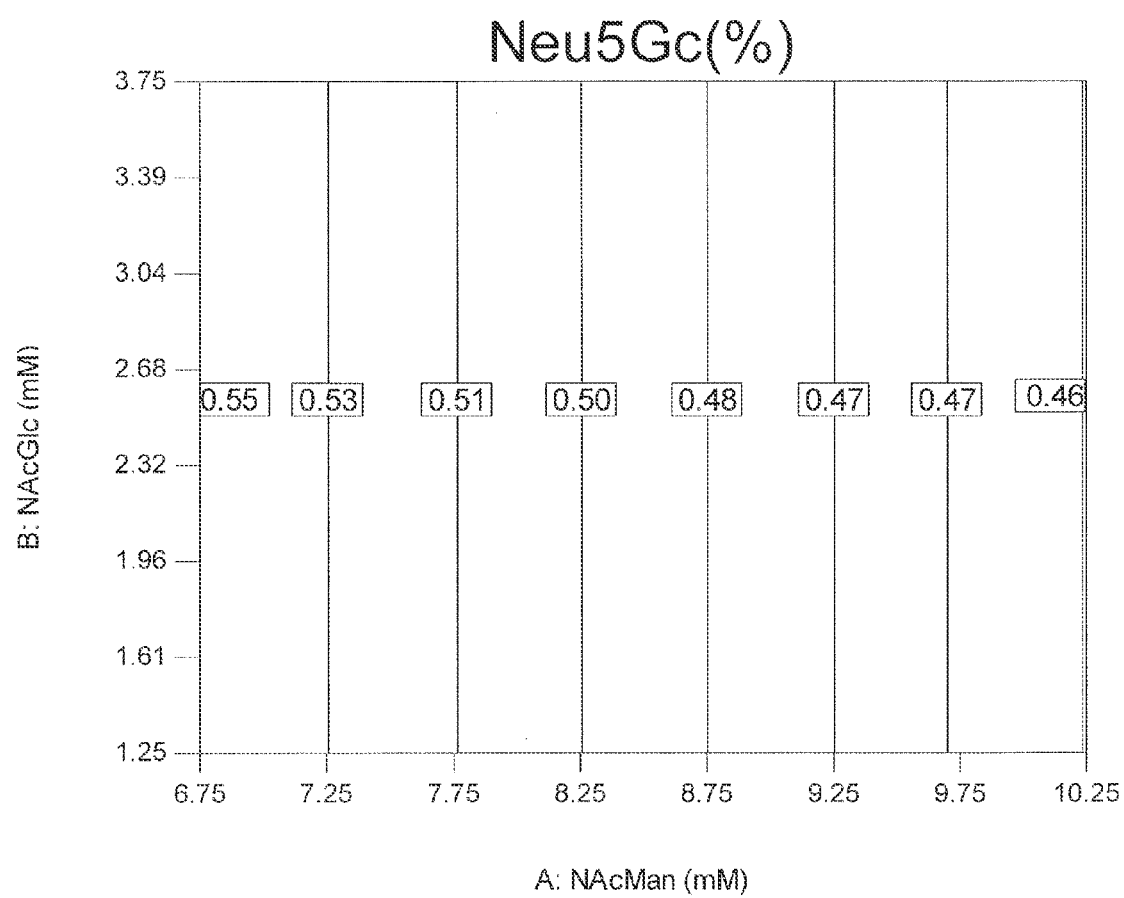
FIG. 7 depicts a contour diagram presenting the Neu5Gc content in the presence of both NAcMan and NAcGlc in the medium.
Figure 8:
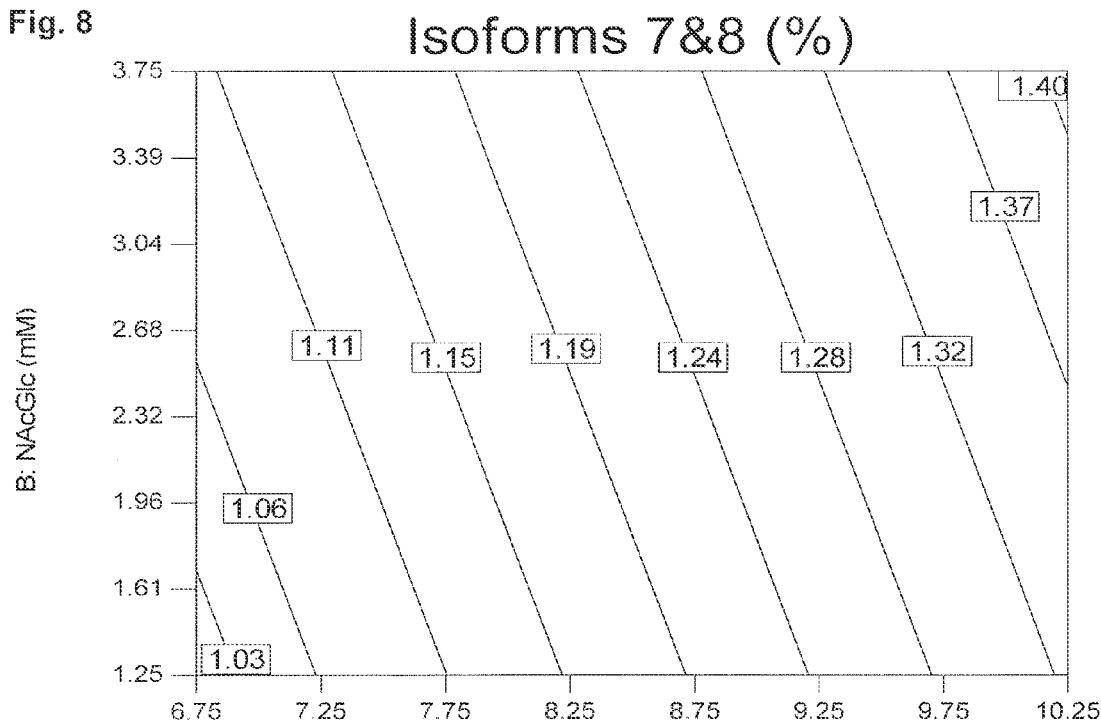
FIG. 8 depicts a contour diagram presenting the content of the most acidic isoforms 7 and 8 in the presence of both NAcMan and NAcGlc in the medium.
Figure 9:
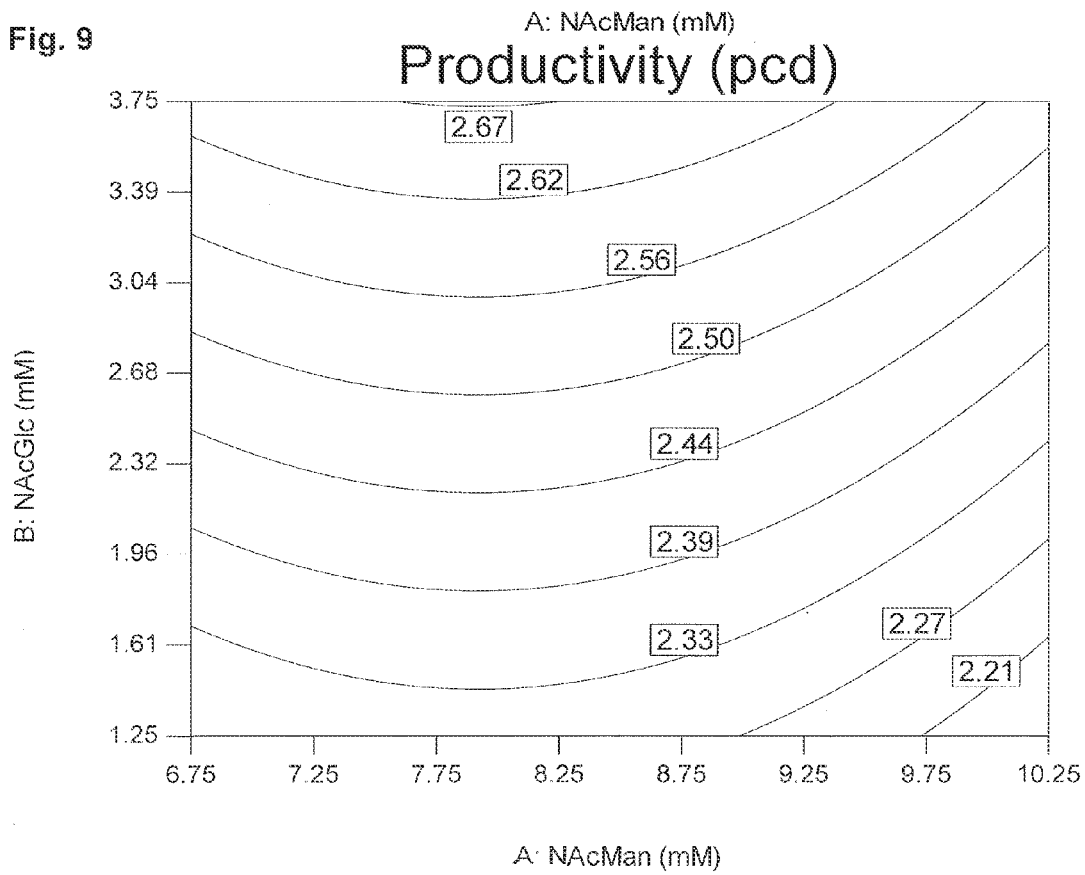
FIG. 9 depicts a contour diagram presenting the specific productivity (abbreviated as Qp and expressed in pg of protein/glycoprotein per cell per day (pcd)) in the presence of both NAcMan and NAcGlc in the medium.

By using NAcMan in a concentration of above 8 or even 8.50 mM and NAcGlc in a concentration of 1.25 mM to 3.75 mM, the Neu5Gc content was reduced to even below 0.5% (with a minimum of 0.46% when using 10.25 mM NAcMan, FIG. 7). The content of the most acidic isoforms (e.g., of isoforms 7 and 8) simultaneously increased to figures as high as 1.23%, and even higher. The maximal content of the most acidic isoforms (1.40%) was achieved by supplementing media with 10.25 mM NAcMan and 3.75 mM NAcGlc (FIG. 8). Both supplements, NAcMan and NAcGlc, effected also the specific productivity, which was slightly increased with increasing NAcGlc concentrations (from averaged 2.21 pcd in media with 1.25 mM NAcGlc to averaged 2.62 pcd in media with NAcGlc above 3.5 mM).

After analysing all results, numerical optimisation with DOE programme was performed. A decreased Neu5Gc content and an increased content of the most acidic isoforms were selected as the most important parameters and productivity as a medium-important parameter. DOE calculated 48 combinations with the lowest desirability of 0.344. The most desirable combination is presented in Table 2, and DOE programme calculated that, by using 9.94 mM NAcMan and 3.75 mM NAcGlc, the Neu5Gc content will be within the confidential (predicted) interval. In case of the confidential interval, the content of Neu5Gc will be in the range of 0.37% to 0.49%. In case of the predicted interval, the content of Neu5Gc will range from 0.34% to 0.53%, however. Quite conversely, the content of the most acidic isoforms is within the confidential interval of 1.22% to 1.46% and within the predicted interval of 1.05% to 1.63%, respectively. In 47 other combinations calculated by the programme, selected NAcMan concentrations were between 8.18 mM and 10.25 mM and selected NAcGlc concentrations between 1.25 mM and 3.75 mM. By using different combinations of NAcMan and NAcGlc, the average Neu5Gc content is predicted to be in the range of 0.43% to 0.48%. The average content of the most acidic isoforms is predicted to be in the range of 1.14% to 1.36% (Table 3).

Therefore, one can conclude that media supplemented with 6.75 mM to 10.25 mM NAcMan and with 1.25 mM to 3.75 mM NAcGlc will result in a significantly decreased Neu5Gc content (below 0.55%). Despite the decreased Neu5Gc content, improvement of the sialylation pattern (the content of the most acidic isoforms will be 1.03% or even higher) is concomitantly achieved without negatively affecting productivity. Table 3 does not depict the figure of 0.55%, since only mean values for the content of Neu5Gc are presented. 0.55% is the highest of all predicted intervals (95% PI high). Also, the figure of 1.03% is nowhere presented in Table 3. Again, the reason is that only mean values for isoforms 7 and 8 are presented, a content of 1.03% being the lowest content of the predicted intervals (95% PI low).

TABLE 2

Calculated confidential intervals (CI) and prediction intervals (PI) when medium was supplemented with 9.94 mM NAcMan and 3.75 mM NAcGlc

| Factor | Name | Level | Low Level | High Level | | | |
|---|---|---|---|---|---|---|---|
| A | NAcMan (mM) | 9.94 | 6.75 | 10.25 | | | |
| B | NAcGlc (mM) | 3.75 | 1.25 | 3.75 | | | |

| Response | Prediction | SE Mean | 95% CI low | 95% CI high | SE Pred | 95% PI low | 95% PI high |
|---|---|---|---|---|---|---|---|
| Productivity (pcd) | 2.33 | 0.14 | 2.05 | 2.62 | 0.29 | 1.74 | 2.93 |
| Neu5Gc (%) | 0.43 | 0.03 | 0.37 | 0.49 | 0.05 | 0.34 | 0.53 |
| Isoforms 7&8 (%) | 1.34 | | 1.22 | 1.46 | | 1.05 | 1.63 |

TABLE 3

48 combinations of NAcMan and NAcGlc concentrations and the corresponding mean values of specific productivity, content of Neu5Gc, and content of the most acidic isoforms, as calculated by the DOE programme.

| NAcMan (mM) | NAcGlc (mM) | Productivity (pcd) | Neu5Gc (%) | Isoforms 7&8 (%) |
|---|---|---|---|---|
| 8.73 | 1.36 | 2.46 | 0.46 | 1.14 |
| 9.57 | 1.25 | 2.42 | 0.44 | 1.17 |
| 9.67 | 1.25 | 2.43 | 0.43 | 1.17 |
| 9.05 | 2.93 | 2.64 | 0.47 | 1.18 |
| 9.90 | 1.25 | 2.38 | 0.43 | 1.19 |
| 9.79 | 1.43 | 2.40 | 0.43 | 1.19 |
| 8.98 | 3.08 | 2.59 | 0.47 | 1.21 |
| 8.84 | 3.75 | 2.81 | 0.48 | 1.21 |
| 10.10 | 2.27 | 2.35 | 0.46 | 1.22 |
| 9.41 | 3.75 | 2.64 | 0.46 | 1.22 |
| 9.39 | 3.75 | 2.63 | 0.46 | 1.22 |
| 9.61 | 3.75 | 2.58 | 0.45 | 1.22 |
| 9.69 | 3.75 | 2.57 | 0.45 | 1.22 |
| 9.59 | 2.79 | 2.41 | 0.44 | 1.23 |
| 9.73 | 3.75 | 2.54 | 0.46 | 1.23 |
| 9.55 | 3.74 | 2.51 | 0.46 | 1.23 |
| 9.16 | 3.75 | 2.62 | 0.46 | 1.23 |
| 9.68 | 3.75 | 2.49 | 0.46 | 1.23 |
| 8.61 | 3.74 | 2.53 | 0.47 | 1.24 |
| 8.18 | 3.27 | 2.51 | 0.47 | 1.24 |
| 9.13 | 3.75 | 2.49 | 0.46 | 1.24 |
| 9.56 | 3.51 | 2.40 | 0.44 | 1.26 |
| 9.64 | 3.69 | 2.40 | 0.44 | 1.26 |
| 9.43 | 3.75 | 2.43 | 0.45 | 1.26 |
| 9.55 | 3.75 | 2.41 | 0.44 | 1.26 |
| 9.58 | 3.75 | 2.40 | 0.44 | 1.26 |
| 9.51 | 3.74 | 2.40 | 0.44 | 1.26 |
| 9.52 | 3.75 | 2.41 | 0.44 | 1.26 |
| 9.68 | 3.75 | 2.38 | 0.44 | 1.27 |
| 9.65 | 3.75 | 2.39 | 0.44 | 1.27 |
| 10.17 | 1.64 | 2.33 | 0.43 | 1.28 |
| 10.07 | 3.75 | 2.48 | 0.46 | 1.28 |
| 10.15 | 1.99 | 2.33 | 0.43 | 1.29 |
| 10.03 | 3.75 | 2.46 | 0.46 | 1.29 |
| 9.97 | 2.31 | 2.34 | 0.44 | 1.30 |
| 9.32 | 3.75 | 2.40 | 0.44 | 1.30 |
| 10.05 | 2.32 | 2.34 | 0.44 | 1.30 |
| 9.82 | 3.74 | 2.37 | 0.44 | 1.30 |
| 10.15 | 3.75 | 2.44 | 0.46 | 1.30 |
| 10.10 | 2.51 | 2.33 | 0.43 | 1.31 |
| 10.25 | 3.75 | 2.40 | 0.45 | 1.31 |
| 9.79 | 3.75 | 2.36 | 0.44 | 1.31 |
| 10.22 | 3.75 | 2.42 | 0.45 | 1.31 |
| 10.02 | 3.72 | 2.32 | 0.44 | 1.32 |
| 9.83 | 3.75 | 2.34 | 0.43 | 1.33 |
| 9.94 | 3.75 | 2.33 | 0.43 | 1.34 |
| 10.25 | 3.75 | 2.33 | 0.44 | 1.34 |
| 10.20 | 3.59 | 2.28 | 0.43 | 1.36 |

Example 7

Effect of NAcMan and NAcGlc on the Neu5Gc Content in Media with Reduced Iron and Insulin Concentration The inventor tested some other medium components like iron, insulin, and glutamine, both in the absence and presence of NAcMan and NAcGlc. She studied the effect of those three components on the Neu5Gc content and degree of sialylation. The result is that a reduced iron concentration entails a reduction of the content of Neu5Gc (roughly, from 1.5 or 2% to only 1%) and a slight increase in the degree of sialylation, calculated on the basis of the increased content of the most acidic isoforms 7 and 8, vs. a higher iron concentration.

The inventor further tested, if there is some additional effect on the reduction of the Neu5Gc content, if medium with reduced iron and insulin concentrations was supplemented with NAcMan and NAcGlc. Two media, non-modified and modified medium (for details, see Table 4 below) were tested for the effect on growth, titres, Neu5Gc content, and content of isoforms 7 and 8 by NAcMan and NAcGlc supplementation.

Repeated batch processes in shake flasks were established, first multiplying cells up to $20 \times 10^6$ viable cells/ml in standard non-modified medium. After 7 days of growth, the exchange with non-modified or modified medium was initiated in two parallel approaches. One set of shake flasks were shaken at 90 rpm, the other at 150 rpm. Other shaking parameters were 37° C. and 10% $CO_2$. Since growth of the cells was better at 150 rpm, later harvests were measured only from cultures obtained following shaking at 150 rpm, whereas only the first harvest (H1) distinguished between 90 and 150 rpm.

TABLE 4

Comparison between non-modified and modified medium

|  | non-modified | modified |
|---|---|---|
| NAcMan | 0 mM | 10.13 mM |
| NAcGlc | 0 mM | 3.75 mM |
| Insulin | 1 mg/L | 0.0123 mg/L |
| Iron | 0.2 mM | 0.077 mM |
| Glutamine | 8 mM | 8.5 mM |
| $MnCl_2 \times 4H_2O$ | 50 µM | 50 µM |

Figure 10A:
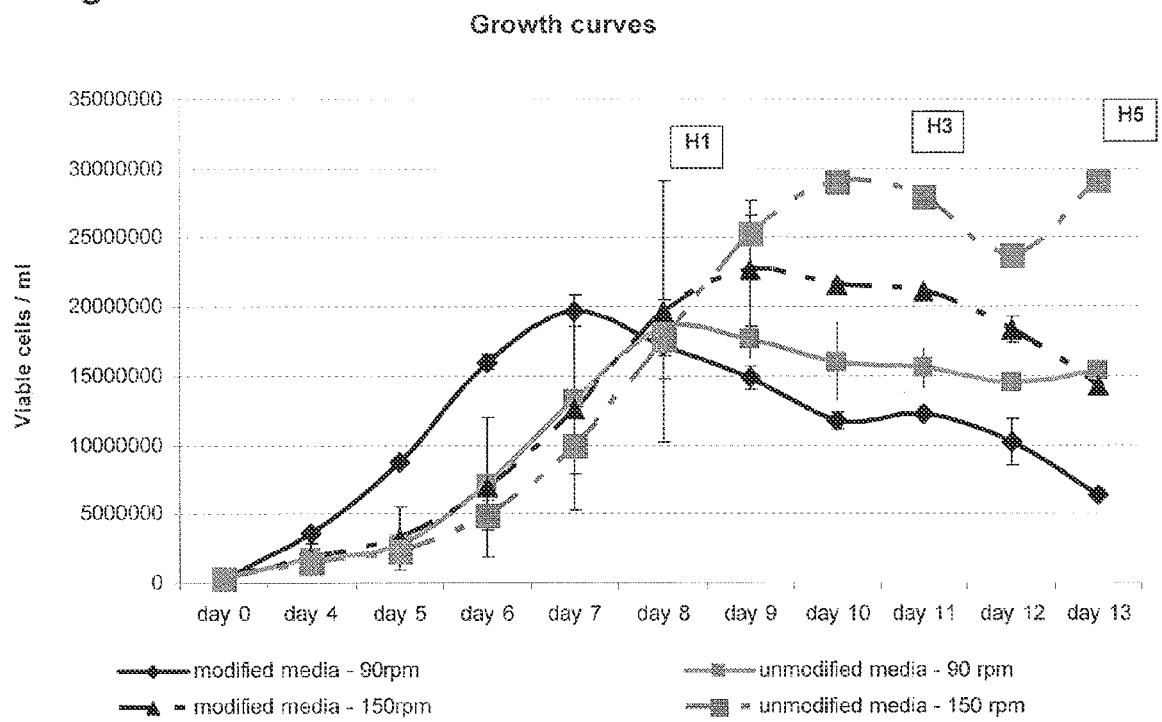
FIG. 10a and FIG. 10b depict the comparison for growth (a) and titre (b) in non-modified (grey) and modified (black) medium when performing shaking in a shaking incubator at 90 rpm and 150 rpm, respectively (for details see Example 7 below).
Figure 10B:
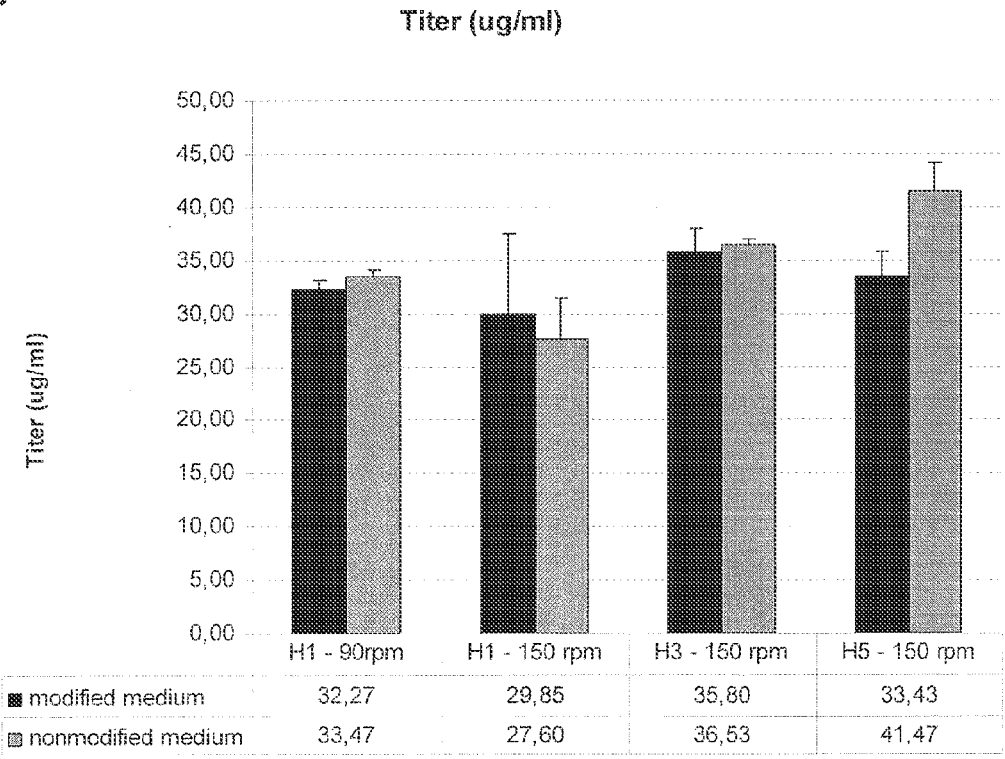

The inventor found that cell growth was better in non-modified medium (FIG. 10a), regardless what the shaking condition was; and cell growth was better at 150 than at 90 rpm (FIG. 10a). Harvests 3 and 5 (H3 and H5) were analysed on days 11 and 13 only in shaking flasks from 150 rpm. Slightly lower titres were generally observed after cultivation in modified medium when compared with unmodified medium, but the overall increase with harvest time was achieved with both media.

The highest degree of sialylation (again estimated via the most acidic isoforms and their content (FIG. 11a) was obtained at 90 rpm in modified medium. In all samples obtained after shaking at 150 rpm, the first unsialylated peak was significantly increased, and the content of the most acidic isoforms generally decreased over time.

In all samples obtained from modified medium, the content of Neu5Gc was significantly lowered by almost or even more than 50%, and that was independent upon shaking at 90 or 150 rpm. Additionally, the decrease of Neu5Gc correlated with the progression of the harvest time. Finally, it was possible to achieve a content of Neu5Gc of as low as 0.2% and even 0.13% with modified medium, once the cells became adapted to that medium (harvest taken on days 11 and 13, FIG. 11b). A typical concentration of NAcMan and NAcGlc was 10.13 mM and 3.75 mM, respectively, in medium with an iron concentration reduced from 0.2 to 0.077 mM and an insulin concentration reduced from 1 to 0.0123 mg/l.

LIST OF REFERENCES CITED

EP-B 1 092 037
EP-B 1 543 106
U.S. Pat. No. 5,459,031
US-A 2007/0161084
Corfield A. P. and Schauer R. (1982) Metabolism of sialic acids, in Cell Biology Monographs, Vol. 10: 5-55.

Gu X and Wang D I C (1998). Improvement of Interferon-γ Sialylation in Chinese Hamster Ovary Cell Culture by Feeding of N-Acetylmannosamine Biotechnology and Bioengineering, 58(6): 642-648.

Schauer R. (2000) Achievements and challenges of sialic acid research. Glycoconjugate Journal 17, 485-499.

Traving C and Schauer R. (1998). Structure, function and metabolism of sialic acids Cell. Mol. Life. Sci. 54: 1330-1349.

Werner R G, Kopp K, Schlueter M. (2007) Glycosylation of therapeutic proteins in different production systems. Acta Pædiatrica 96: 17-22.

Yamaguchi, Shinya; Ohnishi, Jun; Maru, Isafumi; and Ohta, Yasuhiro. (2006). Simple and Large-Scale Production of N-Acetylneuraminic Acid and N-Acetyl-D-Mannosamine. Trends in Glycoscience and Glycotechnology, Vol. 18: 245-252

The invention claimed is:

1. A glycoprotein produced by a method comprising the steps of:
   (a) cultivating eukaryotic cells in a medium comprising the additive DMSO, N- acetylmannosamine (NAcMan), or N-acetylglucosamine (NAcGlc), or any combination of two or more of such additives, wherein the medium additionally comprises iron in a concentration range from 0.05 to 0.1 mM, and
   (b) recovering from that medium, or from said cells, the glycoprotein,
   wherein the glycoprotein exhibits (i) a degree of sialylation increased by at least 5%, when compared with the degree of sialylation of the same glycoprotein when produced in the same medium but without the additive or additives; and (ii) a content of Neu5Gc (N- glycolylneuraminic acid) that is at least 50% lower than the content of Neu5Gc of the same glycoprotein when produced in the same medium but without the additive or additives.

2. The glycoprotein of claim 1, wherein the glycoprotein exhibits a degree of sialylation increased by at least 10%, 15%, 20%, 25%, or 30%.

3. The glycoprotein of claim 1, wherein the glycoprotein exhibits a decreased content of Neu5Gc by at least 60%, 70%, 80%, 90%, or 99%.

4. The glycoprotein of claim 1, wherein the combination of additives comprises NAcMan and NAcGlc.

5. The glycoprotein of claim 4, wherein the medium further comprises $Mn^{2+}$.

6. The glycoprotein of claim 4, wherein DMSO ranges in concentration from 0.25 to 1.5% (w/v), in particular wherein the concentration of DMSO ranges from 0.45 to 1.25 or from 0.65 to 1% (w/v), or wherein the concentration of DMSO is 0.75% (w/v).

7. The glycoprotein of claim 1, wherein the medium comprises DMSO.

8. The glycoprotein of claim 1, wherein the iron concentration is 0.070 to 0.09 mM.

9. The glycoprotein of claim 1, wherein the iron concentration is 0.075 to 0.08mM.

10. The glycoprotein of claim 1, wherein the medium further comprises $Mn^{2+}$.

11. The glycoprotein of claim 10, wherein the $Mn^{2+}$ concentration ranges from 30 to 250, from 50 to 200, from 80 to 180, or from 100 to 150 μm.

12. The glycoprotein of claim 10, wherein the concentrations of NAcMan and NAcGlc in the medium range independently from 3 to 20 mM.

13. The glycoprotein of claim 12, wherein the concentrations of NAcMan and NAcGlc in the medium range independently from 5 to 10 mM.

14. The glycoprotein of claim 12, wherein the concentrations of NAcMan and NAcGlc are 8.75 mM.

15. The glycoprotein of claim 10, wherein the $Mn^{2+}$ concentration in the medium ranges from 30 to 250, from 50 to 200, from 80 to 180, or from 100 to 150 μM.

16. The glycoprotein of claim 1, wherein the medium comprises DMSO.

17. The glycoprotein of claim 1, wherein the concentration of iron is 0.077 mM.

* * * * *